United States Patent
Chang et al.

(10) Patent No.: US 9,707,238 B2
(45) Date of Patent: *Jul. 18, 2017

(54) OIL-IN-WATER METHOD FOR MAKING POLYMERIC IMPLANTS CONTAINING A HYPOTENSIVE LIPID

(71) Applicant: Allergan, Inc., Irvine, CA (US)

(72) Inventors: James Chang, Newport Beach, CA (US); Patrick Hughes, Aliso Viejo, CA (US); Chin-Ming Chang, Tustin, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/822,646

(22) Filed: Aug. 10, 2015

(65) Prior Publication Data

US 2016/0015718 A1 Jan. 21, 2016

Related U.S. Application Data

(60) Continuation of application No. 14/228,020, filed on Mar. 27, 2014, now Pat. No. 9,101,583, which is a
(Continued)

(51) Int. Cl.
*A61K 31/165* (2006.01)
*A61K 31/5575* (2006.01)
(Continued)

(52) U.S. Cl.
CPC ........ *A61K 31/5575* (2013.01); *A61K 9/0048* (2013.01); *A61K 9/0051* (2013.01);
(Continued)

(58) Field of Classification Search
CPC .. A61K 31/165; A61K 9/1694; A61K 9/0048; A61K 9/0051; A61K 9/107;
(Continued)

(56) References Cited

U.S. PATENT DOCUMENTS 3,396,081 A    8/1968   Billek at al
3,749,776 A    7/1973   Eakins at al
(Continued)

FOREIGN PATENT DOCUMENTS

CA    1333770    1/1995
EP    0251680    1/1988
(Continued)

OTHER PUBLICATIONS

Allergan, Alphagan Product Information, Product Sheet, 2005, 1-10.
(Continued)

*Primary Examiner* — Carlos Azpuru
(74) *Attorney, Agent, or Firm* — Laura L. Wine

(57) ABSTRACT

Biocompatible microparticles include an ophthalmically active cyclic lipid component and a biodegradable polymer that is effective, when placed into the subconjunctival space, in facilitating release of the cyclic lipid component into the anterior and posterior segments of an eye for an extended period of time. The cyclic lipid component can be associated with a biodegradable polymer matrix, such as a matrix of a two biodegradable polymers. Or, the cyclic lipid component can be encapsulated by the polymeric component. The present microparticles include oil-in-water emulsified microparticles. The subconjunctivally administered microparticles can be used to treat or to reduce at least one symptom of an ocular condition, such as glaucoma or age related macular degeneration.

12 Claims, 10 Drawing Sheets

Related U.S. Application Data division of application No. 11/371,118, filed on Mar. 8, 2006, now Pat. No. 8,722,097, which is a continuation-in-part of application No. 11/368,845, filed on Mar. 6, 2006, now abandoned, which is a continuation of application No. 11/303,462, filed on Dec. 15, 2005, now Pat. No. 7,993,634, which is a continuation-in-part of application No. 10/837,260, filed on Apr. 30, 2004, now Pat. No. 7,799,336.

(51) Int. Cl.

| | |
|---|---|
| *A61K 9/16* | (2006.01) |
| *A61K 9/00* | (2006.01) |
| *A61K 47/34* | (2017.01) |
| *B01J 13/04* | (2006.01) |
| *B01J 13/06* | (2006.01) |
| *A61K 9/107* | (2006.01) |
| *A61K 9/14* | (2006.01) |

(52) U.S. Cl.
CPC ............ *A61K 9/107* (2013.01); *A61K 9/1075* (2013.01); *A61K 9/146* (2013.01); *A61K 9/1647* (2013.01); *A61K 9/1694* (2013.01); *A61K 31/165* (2013.01); *A61K 47/34* (2013.01); *B01J 13/04* (2013.01); *B01J 13/06* (2013.01)

(58) Field of Classification Search
CPC .. A61K 9/146; A61K 9/1647; A61K 31/5575; A61K 47/34; B01J 13/04; B01J 13/06
See application file for complete search history.

(56) References Cited

U.S. PATENT DOCUMENTS

| | | |
|---|---|---|
| 3,845,770 A | 11/1974 | Theeuwes et al. |
| 3,916,899 A | 11/1975 | Theeuwes et al. |
| 4,008,864 A | 2/1977 | Torphammar et al. |
| 4,014,335 A | 3/1977 | Arnold |
| 4,052,505 A | 10/1977 | Higuchi et al. |
| 4,057,619 A | 11/1977 | Higuchi et al. |
| 4,063,064 A | 12/1977 | Saunders et al. |
| 4,088,864 A | 5/1978 | Theeuwes et al. |
| 4,144,317 A | 3/1979 | Higuchi et al. |
| 4,158,005 A | 6/1979 | Bodor et al. |
| 4,186,184 A | 1/1980 | Zaffaroni |
| 4,190,642 A | 2/1980 | Gale et al. |
| 4,200,098 A | 4/1980 | Ayer et al. |
| 4,281,654 A | 8/1981 | Shell et al. |
| 4,285,987 A | 8/1981 | Ayer et al. |
| 4,303,637 A | 12/1981 | Shell et al. |
| 4,304,765 A | 12/1981 | Shell et al. |
| 4,327,725 A | 5/1982 | Cortese |
| 4,396,625 A | 8/1983 | Yamamori et al. |
| 4,425,346 A | 1/1984 | Horlington et al. |
| 4,454,151 A | 6/1984 | Waterbury |
| 4,474,451 A | 10/1984 | Mizokami |
| 4,478,818 A | 10/1984 | Shell et al. |
| 4,494,274 A | 1/1985 | Thurlow |
| 4,521,210 A | 6/1985 | Wong |
| 4,599,353 A | 7/1986 | Bito |
| 4,649,151 A | 3/1987 | Dougherty et al. |
| 4,656,186 A | 4/1987 | Bommer et al. |
| 4,668,506 A | 5/1987 | Bawa |
| 4,675,338 A | 6/1987 | Bommer et al. |
| 4,693,885 A | 9/1987 | Bommer et al. |
| 4,712,500 A | 12/1987 | Montandon |
| 4,853,224 A | 8/1989 | Wong |
| 4,863,457 A | 9/1989 | Lee |
| 4,865,846 A | 9/1989 | Kaufman |
| 4,866,168 A | 9/1989 | Dougherty et al. |
| 4,932,934 A | 6/1990 | Dougherty et al. |
| 4,932,984 A | 6/1990 | Nankee et al. |
| 4,935,498 A | 6/1990 | Sessler et al. |
| 4,959,217 A | 9/1990 | Sanders et al. |
| 4,968,715 A | 11/1990 | Dougherty et al. |
| 4,981,871 A | 1/1991 | Abelson |
| 4,997,652 A | 3/1991 | Wong |
| 5,002,962 A | 3/1991 | Pandey et al. |
| 5,017,579 A | 5/1991 | Gubin et al. |
| 5,019,400 A | 5/1991 | Gombotz et al. |
| 5,028,621 A | 7/1991 | Dougherty et al. |
| 5,028,624 A | 7/1991 | Chan et al. |
| 5,034,413 A | 7/1991 | Chan et al. |
| 5,075,115 A | 12/1991 | Brine |
| 5,089,509 A | 2/1992 | Chandraratna |
| 5,093,349 A | 3/1992 | Pandey et al. |
| 5,100,431 A | 3/1992 | Buster et al. |
| 5,164,188 A | 11/1992 | Wong |
| 5,166,331 A | 11/1992 | Della Valle |
| 5,169,638 A | 12/1992 | Dennis et al. |
| 5,171,741 A | 12/1992 | Dougherty |
| 5,173,504 A | 12/1992 | Dougherty |
| 5,190,966 A | 3/1993 | Dougherty et al. |
| 5,198,460 A | 3/1993 | Pandey et al. |
| 5,268,178 A | 12/1993 | Calhoun et al. |
| 5,300,114 A | 4/1994 | Gwon et al. |
| 5,314,905 A | 5/1994 | Pandey et al. |
| 5,356,629 A | 10/1994 | Sander et al. |
| 5,378,475 A | 1/1995 | Smith |
| 5,384,333 A | 1/1995 | Davis et al. |
| 5,385,887 A | 1/1995 | Yim et al. |
| 5,438,071 A | 8/1995 | Clauss et al. |
| 5,443,505 A | 8/1995 | Wong et al. |
| 5,459,159 A | 10/1995 | Pandey et al. |
| 5,466,233 A | 11/1995 | Weiner et al. |
| 5,501,856 A | 3/1996 | Ohtori et al. |
| 5,504,074 A | 4/1996 | D'Amato et al. |
| 5,516,522 A | 5/1996 | Peyman et al. |
| 5,523,301 A | 6/1996 | Amon et al. |
| 5,585,401 A | 12/1996 | Brandt et al. |
| 5,587,371 A | 12/1996 | Sessler et al. |
| 5,587,479 A | 12/1996 | Makovec et al. |
| 5,597,897 A | 1/1997 | Ron et al. |
| 5,612,364 A | 3/1997 | York et al. |
| 5,655,832 A | 8/1997 | Pelka et al. |
| 5,656,297 A | 8/1997 | Bernstein et al. |
| 5,688,819 A | 11/1997 | Woodward et al. |
| 5,707,643 A | 1/1998 | Ogura |
| 5,716,981 A | 2/1998 | Hunter et al. |
| 5,766,242 A | 6/1998 | Wong et al. |
| 5,770,589 A | 6/1998 | Billson et al. |
| 5,776,699 A | 7/1998 | Klein et al. |
| 5,798,349 A | 8/1998 | Levy et al. |
| 5,824,072 A | 10/1998 | Wong |
| 5,824,074 A | 10/1998 | Koch |
| 5,869,079 A | 2/1999 | Wong et al. |
| 5,877,207 A | 3/1999 | Klein et al. |
| 5,882,682 A | 3/1999 | Rork et al. |
| 5,906,920 A | 5/1999 | Evans et al. |
| 5,913,884 A | 6/1999 | Trauner et al. |
| 5,919,970 A | 7/1999 | Song et al. |
| 5,922,773 A | 7/1999 | Lipton et al. |
| 5,958,954 A | 9/1999 | Klein et al. |
| 5,965,152 A | 10/1999 | Galin et al. |
| 5,972,326 A | 10/1999 | Galin et al. |
| 6,051,576 A | 4/2000 | Ashton et al. |
| 6,066,675 A | 5/2000 | Wen et al. |
| 6,074,661 A | 6/2000 | Olejnik et al. |
| 6,217,869 B1 | 4/2001 | Meyer et al. |
| 6,217,895 B1 | 4/2001 | Guo et al. |
| 6,225,303 B1 | 5/2001 | Miller et al. |
| 6,258,319 B1 | 7/2001 | Hearst et al. |
| 6,270,492 B1 | 8/2001 | Sinofsky |
| 6,270,749 B1 | 8/2001 | Blumenkranz et al. |
| 6,271,220 B1 | 8/2001 | Garst et al. |
| 6,274,614 B1 | 8/2001 | Richter et al. |
| 6,290,713 B1 | 9/2001 | Russell |
| 6,294,361 B1 | 9/2001 | Horowitz et al. |
| 6,306,426 B1 | 10/2001 | Olejnik et al. |
| 6,309,669 B1 | 10/2001 | Setterstrom et al. |
| 6,317,616 B1 | 11/2001 | Glossop |

(56) References Cited

U.S. PATENT DOCUMENTS

| | | |
|---|---|---|
| 6,319,273 B1 | 11/2001 | Chen et al. |
| 6,331,313 B1 | 12/2001 | Wong et al. |
| 6,357,568 B1 | 3/2002 | Chen |
| 6,369,116 B1 | 4/2002 | Wong et al. |
| 6,395,787 B1 | 5/2002 | Woodward et al. |
| 6,403,649 B1 | 6/2002 | Woodward |
| 6,455,062 B1 | 9/2002 | Olejnik et al. |
| 6,482,854 B1 | 11/2002 | Lipton et al. |
| 6,497,729 B1 | 12/2002 | Moussy et al. |
| 6,537,568 B2 | 3/2003 | Olejnik et al. |
| 6,548,078 B2 | 4/2003 | Guo et al. |
| 6,565,871 B2 | 5/2003 | Roser et al. |
| 6,573,280 B2 | 6/2003 | Dreyer |
| 6,595,945 B2 | 7/2003 | Brown |
| 6,699,493 B2 | 3/2004 | Wong |
| 6,713,081 B2 | 3/2004 | Robinson et al. |
| 6,726,918 B1 | 4/2004 | Wong et al. |
| 6,765,012 B2 | 7/2004 | Andrews et al. |
| 6,899,717 B2 | 5/2005 | Weber et al. |
| 7,091,231 B2 | 8/2006 | Donde |
| 7,476,747 B2 | 1/2009 | Old |
| 7,589,057 B2 | 9/2009 | Chang et al. |
| 7,592,364 B2 | 9/2009 | Old et al. |
| 7,771,742 B2 | 8/2010 | Hughes et al. |
| 7,799,336 B2 | 9/2010 | Hughes et al. |
| 7,820,661 B2 | 10/2010 | Old et al. |
| 7,993,634 B2 * | 8/2011 | Hughes ............... A61K 9/0051 424/78.04 |
| 8,119,154 B2 | 2/2012 | Huang et al. |
| 8,147,865 B2 | 4/2012 | Huang et al. |
| 8,206,736 B2 | 6/2012 | Hughes |
| 8,206,737 B2 | 6/2012 | Hughes |
| 8,293,210 B2 | 10/2012 | Huang et al. |
| 8,445,027 B2 | 5/2013 | Hughes |
| 8,647,659 B2 | 2/2014 | Robinson et al. |
| 8,673,341 B2 | 3/2014 | Hughes |
| 8,722,097 B2 | 5/2014 | Chang et al. |
| 8,911,767 B2 | 12/2014 | Hughes |
| 8,969,415 B2 | 3/2015 | Robinson et al. |
| 9,006,464 B2 | 4/2015 | Donde et al. |
| 9,101,583 B2 * | 8/2015 | Chang ................ A61K 9/0051 |
| 2001/0023363 A1 | 9/2001 | Harth et al. |
| 2002/0032201 A1 | 3/2002 | Olejnik |
| 2002/0035264 A1 | 3/2002 | Kararli |
| 2002/0040015 A1 | 4/2002 | Miller et al. |
| 2002/0094998 A1 | 7/2002 | Burke et al. |
| 2002/0103255 A1 | 8/2002 | Hellberg et al. |
| 2003/0018078 A1 | 1/2003 | Woodward et al. |
| 2003/0069286 A1 | 4/2003 | Chen et al. |
| 2003/0069560 A1 | 4/2003 | Adamis et al. |
| 2003/0095995 A1 | 5/2003 | Wong et al. |
| 2003/0185873 A1 | 10/2003 | Chasin et al. |
| 2003/0199478 A1 | 10/2003 | Andrews et al. |
| 2003/0220376 A1 | 11/2003 | Masferrer |
| 2003/0225152 A1 | 12/2003 | Andrews et al. |
| 2004/0054374 A1 | 3/2004 | Weber et al. |
| 2004/0058313 A1 | 3/2004 | Abreu |
| 2004/0127843 A1 | 7/2004 | Tu |
| 2004/0137059 A1 | 7/2004 | Nivaggioli |
| 2004/0151753 A1 | 8/2004 | Chen et al. |
| 2004/0208910 A1 | 10/2004 | Ashton et al. |
| 2004/0234611 A1 | 11/2004 | Ahlheim et al. |
| 2005/0003007 A1 | 1/2005 | Boix et al. |
| 2005/0107463 A1 | 5/2005 | Woodward |
| 2005/0112175 A1 | 5/2005 | Yaacobi |
| 2005/0113806 A1 | 5/2005 | DeCarvalho |
| 2005/0175708 A1 | 8/2005 | Carrasquillo et al. |
| 2005/0192264 A1 | 9/2005 | Penfold |
| 2005/0244458 A1 | 11/2005 | Huang et al. |
| 2005/0244461 A1 | 11/2005 | Nivaggioli et al. |
| 2005/0244462 A1 | 11/2005 | Farooq |
| 2005/0244463 A1 | 11/2005 | Huang |
| 2005/0244464 A1 | 11/2005 | Hughes |
| 2005/0244465 A1 | 11/2005 | Nivaggioli et al. |
| 2005/0244466 A1 | 11/2005 | Whitcup et al. |
| 2005/0244467 A1 | 11/2005 | Nivaggioli et al. |
| 2005/0244468 A1 | 11/2005 | Huang et al. |
| 2005/0244469 A1 | 11/2005 | Whitcup et al. |
| 2005/0244470 A1 | 11/2005 | Hughes et al. |
| 2005/0244471 A1 | 11/2005 | Shiah et al. |
| 2005/0244477 A1 | 11/2005 | Hughes et al. |
| 2005/0244478 A1 | 11/2005 | Hughes et al. |
| 2005/0244479 A1 | 11/2005 | Huang et al. |
| 2005/0244506 A1 | 11/2005 | Burke et al. |
| 2005/0271705 A1 | 12/2005 | Hughes |
| 2006/0013859 A1 | 1/2006 | Yamada et al. |
| 2006/0173060 A1 | 8/2006 | Chang et al. |
| 2006/0182781 A1 | 8/2006 | Hughes |
| 2006/0210604 A1 | 9/2006 | Dadey |
| 2006/0246145 A1 | 11/2006 | Chang |
| 2007/0129552 A1 | 6/2007 | Donde |
| 2007/0142376 A1 | 6/2007 | Fleenor et al. |
| 2007/0203222 A1 | 8/2007 | Old |
| 2007/0224246 A1 | 9/2007 | Hughes et al. |
| 2007/0233037 A1 | 10/2007 | Gifford et al. |
| 2007/0265330 A1 | 11/2007 | Old |
| 2008/0033351 A1 | 2/2008 | Trogden |
| 2008/0131481 A1 | 6/2008 | Hughes |
| 2008/0131482 A1 | 6/2008 | Hughes |
| 2008/0131484 A1 | 6/2008 | Robinson |
| 2008/0145403 A1 | 6/2008 | Spada |
| 2008/0269498 A1 | 10/2008 | Old |
| 2008/0292679 A1 | 11/2008 | Lyons |
| 2008/0312321 A1 | 12/2008 | Donde et al. |
| 2009/0082863 A1 | 3/2009 | Schieber |
| 2009/0124676 A1 | 5/2009 | Donde et al. |
| 2010/0074957 A1 | 3/2010 | Robinson et al. |
| 2010/0098772 A1 | 4/2010 | Robinson et al. |
| 2010/0104654 A1 | 4/2010 | Robinson et al. |
| 2010/0124565 A1 | 5/2010 | Spada et al. |
| 2010/0210689 A1 | 8/2010 | Old et al. |
| 2010/0247606 A1 | 9/2010 | Robinson |
| 2010/0278898 A1 | 11/2010 | Hughes et al. |
| 2010/0310637 A1 | 12/2010 | Abdulrazik et al. |
| 2011/0028523 A1 | 2/2011 | Nguyen et al. |
| 2011/0160210 A1 | 6/2011 | Fleenor et al. |
| 2011/0182966 A1 | 7/2011 | Robinson |
| 2011/0250285 A1 | 10/2011 | Hughes |
| 2012/0219611 A1 | 8/2012 | Hughes |
| 2012/0238633 A1 | 9/2012 | Hughes |
| 2012/0245505 A1 | 9/2012 | Robinson et al. |
| 2013/0071349 A1 | 3/2013 | Robinson et al. |
| 2014/0235681 A1 | 8/2014 | Whitcup et al. |

FOREIGN PATENT DOCUMENTS

| | | |
|---|---|---|
| EP | 0364417 | 9/1989 |
| EP | 0490305 | 6/1992 |
| EP | 0322319 | 8/1992 |
| EP | 0430539 | 10/1994 |
| EP | 1541151 | 6/2005 |
| WO | 94-14417 | 7/1994 |
| WO | 95-13765 | 5/1995 |
| WO | 95-15748 | 5/1995 |
| WO | 95-35097 | 12/1995 |
| WO | 96-38174 | 12/1996 |
| WO | 97-26869 | 7/1997 |
| WO | 99-05263 | 2/1999 |
| WO | 00-04898 | 2/2000 |
| WO | 00/04899 | 3/2000 |
| WO | 00-37056 | 6/2000 |
| WO | 01-30323 | 5/2001 |
| WO | 01-58240 | 8/2001 |
| WO | 02-05815 | 1/2002 |
| WO | 02-09787 | 2/2002 |
| WO | 02/09787 | 2/2002 |
| WO | 02-43785 | 6/2002 |
| WO | 02-085248 | 10/2002 |
| WO | 03-013477 | 2/2003 |
| WO | 03-020172 | 3/2003 |
| WO | 03-024420 | 3/2003 |
| WO | 03-047513 | 6/2003 |
| WO | 03-074038 | 9/2003 |
| WO | 03-103772 | 12/2003 |

(56) References Cited

FOREIGN PATENT DOCUMENTS

| WO | 2004-014352 | 2/2004 |
|---|---|---|
| WO | 2004-019938 | 3/2004 |
| WO | 2009-143288 A1 | 11/2009 |
| WO | 2010-093945 | 8/2010 |

OTHER PUBLICATIONS

Allergen, Inc., Tazorac Product Information Sheet, 2004, 1-8.
AlphaganP, Physician's Desk Reference, Product Information, 54th Edition, 493-494, 2001.
Anderson, Lynne et al, An Injectable Sustained Release Fertility Control System, Contraception, 1976, 375-384, 13.
Andreas, Kristin et al, Biodegradable insulin-loaded PLGA microspheres fabricated by three different emulsification techniques: investigation for cartilage tissue engineering, Acta Biomaterialia, 2011, 1485-1495, 7.
Arshady, Reza, Preparation of biodegradable microspheres and microcapsules: 2. Polyactides and related polyesters, J. Controlled Release, 1991, 1-22, 17.
Baker, Richard, Controlled Release of Biologically Active Agent, A Wiley, 1987, 73-75, Interscience Publication.
Bito, Laszlo, A new approach to the medical management of glaucoma, from the bench to the clinic, and beyond, Investigative Ophthalmology & Visual Science, 2001, 1126-1133, 42(6), The Proctor Lecture.
Bito, LZ, Biological Protection with Prostanoids, CRC Press, Inc., 1985, 231-252, 1, Cohen, M. M., ed., Boca Raton, Fla.
Bito, LZ, Prostaglandins, Old Concepts and New Perspectives, Archives of Ophthalmology, 1987, 1036-1039, 105.
Bito, LZ, Prostaglandins, Other Eicosanoids, and Their derivatives as Potential Antiglaucoma Agents, Glaucoma: Applied Pharmacology, 1984, 477-505, 20.
Bodor, Nicholas et al, A Comparison of Intraocular Pressure Elevating Activity of Loteprednoletabonate and Dexamethasone in Rabbits, Current Eye Research, 1992, 525-530, 11.
Brubaker, Richard, Mechanism of Action of Bimatoprost (Lumigan™), Surv Ophthalmol, 2001, S347-S351, 45—Suppl 4.
Busse, Dagmar et al, Tyrosine Kinase Inhibitors: Rationale, Mechanisms of Action, and Implications for Drug Resistance, Semin Oncol, 2001, 47-55, 28—Suppl 16.
Camras, C.B., Reduction of Intraocular Pressure by Prostaglandins Applied topically to the Eyes of Conscious Rabbits, Investigative Ophthalmology & Visual Science, Dec. 1977, 1125-1134, 16(12), US.
Cantor, LB, An Update on Bimatoprost in Glaucoma Therapy, Expert Opin Pharmacother, Dec. 2002, 1753-1762, 3 (12).
Casser, Linda et al, Subconjunctival Injection, Atlas of Primary Eyecare Procedures, 1997, 432-435, 2.
Cen, Jie et al, Preliminary evaluation of biodegradable implant for intraocular sustained-release of cefuroxime in rabbits, Journal of Shanghai Jiaotong, Jun. 2008, 644-647, 28(6).
Charles, Jean-Bernard et al., Use of Bioerodible Polymers Impregnated with Mitomycin in Glaucoma Filtration Surgery in Rabbits, Ophthalmology, Apr. 1991, 503-508, 98-4.
Chen, June et al, LumiganR: A Novel Drug for Glaucoma Therapy, Optom in Pract., Jun. 12, 2002, 95-102, 3.
Cheng, Cheng-Kuo et al., Intravitreal Sustained-Release Dexamethasone Device in the Treatment of Experimental Uveites, Investigative Ophthalmology & Visual Science, 1995, 442-453, 96 (2), US.
Chiang, Chiao-Hsi et al, Pharrnacokinetics and Intraocular Pressure Lowering Effect of Timolol Preparations in Rabbit Eyes, Journal of Ocular Pharmacology and Therapeutics, 1996, 471-480, 12(4).
Clive, Migdal, Lumigan(R): A New Ocular Hypotensive Agent for Achieving Target Intraocular Pressure, Acta Ophthalmol Scand Scientific Abstracts, 2002, 457, 80-4.
Coleman, Anne et al, A 3-Month Randomized Controlled Trial of Bimatoprost (LUMIGAN) Versus Combined Timolol and Dorzolamide (Cosopt) in Patients with Glaucoma or Ocular Hypertension, Ophthalmology, 2003, 2362-8, 110-12.
Coquelet, P. et al, Successful Photodynamic Therapy Combined with Laser Photocoagulatio in Three Eyes With Classic Subfoveal Choroidal Neovascularisation Affecting Two Patients With Multifocal Choroiditis: Case Reports, Bull, Soc. Beige Ophthalmal, 2002, 69-73, 283.
Di Colo, Giacomo, Controlled Drug Release From Implantable Matrices Based on Hydrophobic Polymers, Biomaterials, 1992, 850-856, 13(12).
Dorlands Medical Dictionary, Analogue, Dorlands Medical Dictionary, 2009, 2 pages, US.
Doucet, O. et al, O/W emulsion and W/O/W multiple emulsion: physical characterization and skin pharmacokinetic comparison in the delivery process of caffeine, Int. J. Cosmetic Scient, 1998, 283-295, 20.
Enyedi, Laura et al, An intravitreal Device Providing Sustained Release of Cyclosporins and Dexamethason, Current Eye Research, 1996, 549-557.
Epstein, David, Primary Open-Angle Glaucoma, Chandler and Grant's Glaucoma, 1986, 129-181.
Fabbro, Doriano et al, Protein Kinase Inhibitors: New Treatment Modalities?, Curent Opinion in Pharmacology, 2002, 374-381, 2.
Fotsis, Theodore et al, The Endogenous Oestrogen Metabolite 2-methoxyoestradiol inhibits Angiogeneses and Suppresses Tumour Growth, Current Opinion in Pharmacology, 1994, 368, 237.
Gennaro, Remington, Ophthalmic Preparations—Vehicles, The Science and Practice of Pharmacy, 2000, 827 20th Edition.
Gil, Dan et al, Molecular characterization and ocular hypotensive effects of prostanoid EP2 receptors, Exp Eye Res, Sep. 1996, S104—Abstract 5, 63(Suppl 1).
Goel, Sanjay et al, Tyrosine Kinase Inhibitors: A Clinical Perspective, Current Oncology Reports, 2002, 9-19, 4.
Guenther, Lyn, Optimizing Treatment with Topical Tazarotene, Am. J. Clin. Demiotol, 2003, 197-202, 4-3.
Hainsworth, Dean et al, Sustained Release Intravitreal Dexamethasone, Journal of Ocular Pharmacology and Therapeutics, 1996, 57-63, 12-1.
Haluska, Paul et al, Receptor tyrosine kinase inhibitors, Current Opinion in Investigational Drugs, 2001, 280-286, 2-2.
Hare, William et al, Efficacy and Safety of Memantine, an NMDA-Type Open-Channel Blocker, from Reduction of Retinal Injury associated with Experimental Glaucoma in Rat and Monkey, Sur Ophthalmol, 2001, S284-S289, 45—Suppl. 3.
Hashizoe, Mototane et al, Scleral Plugof Biodegradable Polymers for Controlled Drug Release in the Vitreous, Arch Ophthalmol, 1994, 1380-1384, 112.
Haynes, Robert Jr, Adrenocorticotropic Hormone; Adrenocortical Steroids and Their Synthetic Analogs; Inhibitors of the Synthesis and Actions of Adrenocotical Hormones, The Pharmacological Basis of Therapeutics, 1990, 1431-1462, 8th Edition.
Heller, J., Hydrogels in Medicine and Pharmacy, N.A. Peppes ed., 1987, 137-149.
Heller, Jorge, Biodegradable Polymers in Controlled Drug Delivery, Critical Reviews in Therapeutic Drug Carrier Systems, 1987, 39-90, 1 (1).
Herrero-Vanrell, Rocio et al, Biodegradable Microspheres for Vitreoretinal Drug Delivery, Advanced Drug Delivery, 2001, 5-16, 52, US.
Heys, J., A Boussinesq Model of Natural Convection in the Human Eye and the Formaton of Krukenberg's Spindle, Annals of Biomedical Engineering, 2002, 392-401, 30.
Higginbotham, Eve et al, One-Year, Randomized Study Comparing Bimatoprost and Timolol in Glaucoma and Ocular Hypertension, Archives of Ophthalmology, Oct. 2002, 1286-1293, 120 (10), US.
Hoyng, Philip et al, Pharmacological Therapy for Glaucoma, Drugs 2000, 2000, 411-434, 59 (3), US.
Hsu, Wei-Cherng et al, Tissue bioengineering for surgical bleb defects: an animal study, Graefe's Archive for Clinical and Experimental Ophthalmology, 2008, 709-717, 246(5).
Hu, D.N. et al, Effects of prostaglandin E2 and EP receptor agonists on human iridial melanocytes in vitro, Invest Ophthalmol Vis Sci, 2001, S832, 42(4), Abs 4467-B486.

(56) References Cited

OTHER PUBLICATIONS

Hubbard, Stevan et al, Protein Tyrosine Kinase Structure and Function, Annu. Rev. Biochem., 2000, 373-98, 69.
International Search Report and the Written Opinion of the International Searching Authority for International Application No. PCT/US2010/028584, mailed Aug. 3, 2010.
International Search Report dated Jan. 26, 2012, PCT/US2011/021971.
International Search Report received Mar. 28, 2012 in PCT/US2011/032393.
Jackanicz, Theodore et al, Polyactic Acid as a Biodegradable Carrier for Contraceptive Steroids, Contraception, 1973, 227-235, 8-3.
Jain, Rajeev et al, Controlled drug delivery by biodegradable poly(ester) devices: different preparative approaches, Drug Dev. Ind. Pharm, 1998. 703-727, 8.
Jain, Rajeev, The manufacturing techniques of various drug loaded biodegradable poly(lactide-co-glycolide) (PLGA) devices, Biomaterials, 2000, 2475-2490, 21.
Jalil R. et al, Biodegradable poly(lactic acid) and poly(lactide-co-glycolide) microcapsules: problems associated with preparative techniques and release properties, J. Microencapsul., 1990, 297-325, 7(3).
Jalil, R. et al, Micoencapsulaton using poly (L-lactic acid) II: Preparative variables affecting microcapsule properties, J. Microencapsul., 1990, 25-39, 7(1).
Jalil, R. et al, Microencapsulation using poly(L-lactic acid). I: Microcapsule properties affected by the preparative technique, J. Microencapsul., 1989, 473-484, 6(4).
Jampel, Henry et al, Glaucoma Filtration Surgery in Monkeys Using 5-Fluorouridine in Polyanhydride Disks, Arch Ophthalmol, Mar. 1990, 430-435, 108.
Janoria, Kumar et al., Novel Approaches to Retinal Drug Delivery, Expert Opinion Drug Delivery, 2007, 371-388, 4 (4).
Kimura, Hideya et al, A New Vitreal Drug Delivery System Using an Implantable Biodegradable Polymeric Device, Invest Ophthalmol Vis Sci, 1994, 2815-2819, 35.
Kivalo, M. et al, Biodegradable tube implants in experimental glaucoma surgery in the rabbit, Journal of Materials Science: Materials in Medicine, 1999, 53-58, 10.
Kochinke, F. et al, Biodegradable Drug Delivery System for Uveitis Treatment, Investigative Ophthalmology & Visual Science, Feb. 15, 1996, 186-B98, 37(3).
Kumar, Janoria et al, Novel Approaches to Retinal Drug Delivery, Expert Opinion on Drug Delivery, 2007, 371-388, 4.
Kwak, Hyung Woo et al, Evaluation of the Retinal Toxicity and Pharmacokinetics of Dexamethasone After Intravitreal Injection, Arch. Ophthalmol, 1992, 259-66, 110.
Ladewig, M.S. et al, Prostaglandin E1 infusion therapy in dry age-related macular degeneration, Prostaglandins Leukotrienes Essential Fatty Acids, 2005, 251-256, 72.
Lai, Jui-Yang, Biocompatibility Assessment of Gelatin Carriers Used in Corneal Endothelial Cell Delivery, Advances in Condensed Matter and Materials, 2011, 75-96, Chapter 4.
Lai, Jui-Yang, Biocompatibility of chemically cross-liked gelatin hydrogels for ophthalmic use, J. Mater Sci: Mater Med, 2010, 1899-1911, 21.
Lai, Ronald et al, Alpha-2 Adrenoceptor Agonist Protects Retinal Function After Acute Retinal Ischemic Injury in the Rat, Vis Neurosci, 2002, 175-185, 19.
Lee, David et al, Glaucoma Filtration Surgery in Rabbits Using Bioerodible Polymers and 5-Fluorouacil, Ophthalmol, Dec. 1987, 1523-1530, 94-12.
Lee, David et al, The Use of Bioerodible Polymers and 5-Fluorouracils in Glaucoma Filtration Surgery, Ophthalmology & Visual Science, Nov. 1988, 1692-1697, 29-11.
Makadia, Hirenjumar et al, Poly Lactic-co-Glycolic Acid (PLGA) as Biodegradable Controlled Drug Delivery Carrier, Polymers (Basel), 2011, 1377-1397, 3(3).
Marks, R., Topical Tazarotene:Review and Re-Evaluation, Retinoids, 2001, 72-74, 17(3).

Maruquis, Robert et al., Management of Glaucoma: Focus on Pharmacological Therapy, Drugs & Aging, 2005, 1-21, 22 (1).
Maurice, David, Micropharmaceutics of the Eye, Ocular Inflammation Ther., 1983, 97-102, 1.
Mayo Clinic Com, Stargardt's Disease: Can It Be Treated?, May 27, 2008, 2 Pages.
Merck Source, Analogue, Dorland's Medical Dictionary, 2007, 2 pages.
Miller, Robert et al, Degradation Rates of Oral Resorbable Implants (Polyactates and Polyglycolates): Rate Modification with Changes in PLA/PGA Copolymer Ratios, J. Biomed Materials Res, 1977, 711-719, 11.
Miller, Thomas et al, Synthesis and Structure-Activity Profiles of A-Homoestranes, the Estratopones, J. Med. Chem., 1997, 3836-3841, 40.
Moshfeghi, Darius et al, Retinal and Choroidal Vascular Occlusion After Posterior Sub-Tenon Triamcinolone Injection, American Journal of Ophthalmology, 2002, 132-134, vol. 134.
Moss, Kate, Leber's Congenital Amaurosis, TSBVI, Texas Deafblind Outrech, Apr. 27, 2008, 3 Pages, US.
Muther, Philipp Sebastian, Development of a Resorable Anterior Chamber Glaucoma Implant, Dissertation-Rheinland-Westfalen Technical College, May 24, 2006, 1-196.
Nam, Y. S. et al, Protein loaded biodegradable microspheres based on PLGA/protein bioconjugates, J. Microencapsulation, 1999, 625-637, 16(5).
Newman, Nancy, Hereditary Optic Neuropathis: From the Mitochondria to the Optic Nerve, American Journal of Ophthalmology, 2005, 517e1-517e8, 140(3), US.
Nilsson, Siv, PGF $2\alpha$ Increases Uveoscleral Outflow, Invest. Ophthalmol. Vis. Sci, 1987, 284, 28 (Suppl).
Nordstrom et al, Persistence and Adherence With Topical Glaucoma Therapy, American Journal of Ophthalmology, 2005, 598-608, 140, US.
Oculex, Oculex Announces Positive Clinical Results for Posurdex(r) the first biodegradable ocular implant, PR Newswire, Aug. 6, 2002, 1-2.
Olsen, Timothy et al, Human Scleral Permeability: Effects of Age, Cryotherapy, Transcleral Diode Laser, and Surgical Thinning, Invest. Ophthalmol. Vis, Sci., 1995, 1893-1903, 36.
Phillips, Calbert et al, Penetration of Timolol Eye Drops into Human Aqueous Humor: The First Hour, British Journal of Ophthalmology, 1985, 217-218, 69.
Phillips, Tania et al, Efficacy of 0.1% Tazarotene Cream for the treatment of Photodamage, Arch Dermatol, Nov. 2002, 1486-1493, 138(11).
Physician's Desk Reference for Ophthalmic Medicines, 30th Edition, 285-294. 2002.
Pribluda, Victor et al, 2-Methoxyestradiol: An Endogenous Antiangionic and Antiproliferative Drug Candidate, Cancer and Metastasis Reviews, 2000, 173-179, 19.
Quigley, Harry et al, The Mechanism of Optic Nerve Damage in Experimental Acute Intraocular Pressure Elevation, Invest. Ophthalmol. Vis. Sci., 1980, 505-517, 19.
Rao et al, Intraocular Inflammation and Uveitis, Basic and Clinical Science Course; Intraocular Inflammation and Uveitis, 1998-1999, 57-80; 102-103; 152-156, Section 9; Part 2.
Rao et al, Mechanisms of Immune Effector Reactivity, Basic and Clinical Science Course(San Francisco: American Academy of Ophthalmology, 2000-2001, 40-176, 9, Chapter IV.
Renfro, Lisa et al, Ocular Effects of Topical and Systemic Steroids, Dermatologic Clinics, 1992, 505-512, 10.
Schonfeld, David, Lumigan Found Effective in Early Phase 3, Ocul. Surg. News, Mar. 1, 2001, 35, 19(5)1.
Schuettauf, Frank et al, Effects of anti-glaucoma Medications on Ganglion Cell Survival: the DBA/2J Mouse Model, Vision Res., 2002, 2333-2337, 42(20).
Schumacher, Guido et al, The Physiological Estrogen Metabolite 2-Methoxyestradiol Reduced Tumor Growth and Induces Apoptosis in Human Solid Tumors, J Cancer Res Clin Oncol, 2001, 405-410, 127.
Schwartz, Bernard, The Response of Ocular Pressure to Corticosteroids, Ophthamol. Clin. North Am., 1966, 929-989, 6.

(56) References Cited

OTHER PUBLICATIONS

Seah, Steve et al, Use of Surodex in Phacotrabeculectomy Surgery, Am J Ophthalmol, May 2005, 927-928, 139(5).

Shi, Weiyun et al, FK506 in a Biodegradable Glycolide-co-Clatide-co-Caprolactone Polymer for Prolongation of Corneal Allograft Survival, Current Eye Research, 2005, 969-976, 30.

Short, Brian et al, Safety Evaluation of Ocular Drug Delivery Formulations: Techniques and Practical Considerations, Toxicologic Pathology, 2008, 49-62., 36.

Siebold, Earlene et al, Esterified Prostaglandin Shows 'Potent' Promise, Ocular Surgery News, Feb. 1, 1989, pp. 3, 59, 1.

Skalka, Harold et al, Effect of Corticosteroids on Cataract Formation, Arch. Ophthalmol, 1980, 1773-1777, 98.

Smith, Thomas et al, Sustained-Release Subconjunctival 5-Fluorouracil, Ophthalmic Surgery and Laser, Sep. 1996, 763-767, 27-9.

Spaeth George et al, Steroid-Induced Glaucoma: A. Persistent Elevatioin of Intraocular Pressure B. Hisopathological Aspects, Th. Am. Ophth. Soc., 1977, 353-381, vol. LXXV, US.

Starr, Michael, Further Studies on the Effects of Prostagladin on Intraocular Pressure in the Rabbit, Exp. Eye Res., 1971, 170-177, 11.

Stewart, William et al, The Efficacy and Safety of Latanoprost 0.005% Once Daily Versus Brimonidine 0.2% Twice Daily in Open-Angle Glaucoma or Ocular Hypertension, Am J Ophthalmol, May 2001, 631-635, 131.

Tan, Donald et al, Randomized Clinical Trial of a New Dexamethasone Delivery System (Surodex) for Treatment of Post-Cataract Surgery Inflammation, Ophthalmology, Feb. 1999, 223-231, 106 (2).

Tan, Donald et al, Randomized Clinical Trial of Surodex Steroid Drug Delivery System for Cataract Surgery: Anterior Versus Posterior Placement of Two Surodex in the Eye, Ophthalmology, Dec. 2001, 2172-2181, 108(12).

Tazarotene, Drugs Future, 208-209-2003.

The Advanced Glaucoma Intervention Study (AGIS): 7. The relationship between control of intraocular pressure and visual field deterioration, The AGIS Investigators, no authors listed, AM J, Ophthalmol. Oct. 2000; 130(4):429-40, printed from http://ncbi.nlm.nih.gov/pubmed/11024415, 2 pages, abstract only.

Theng, Julian et al, Pharmacokinetic and Toxicity Study of an Intraocular Cyclosporine DDS in the Anterior Segment of Rabbit Eyes, Invest Ophthalmol Vis Sci, Nov. 2003, 4895-4899, 44(11).

Tracy, M.A. et al, Factors Affecting the Degradation Rate of Poly(actide-co-glycolide) Microspheres in Vivo and in Vitro, Biomaterials, 1999, 1057-1062, 20.

U.S. Appl. No. 13/861,688, filed Apr. 12, 2013.
U.S. Appl. No. 10/246,884, filed Sep. 18, 2002.
U.S. Appl. No. 10/259,703, filed Sep. 27, 2002.
U.S. Appl. No. 10/327,018, filed Dec. 20, 2002.
U.S. Appl. No. 10/340,237, filed Jan. 9, 2003.
U.S. Appl. No. 10/836,880, filed Apr. 30, 2004.
U.S. Appl. No. 10/836,904, filed Apr. 30, 2004.
U.S. Appl. No. 10/836,908, filed Apr. 30, 2004.
U.S. Appl. No. 10/837,143, filed Apr. 30, 2004.
U.S. Appl. No. 10/837,142, filed Apr. 30, 2004.
U.S. Appl. No. 10/837,260, filed Apr. 30, 2004.
U.S. Appl. No. 10/837,291, filed Apr. 30, 2004.
U.S. Appl. No. 10/837,348, filed Apr. 30, 2004.
U.S. Appl. No. 10/837,356, filed Apr. 30, 2004.
U.S. Appl. No. 10/837,361, filed Apr. 20, 2004.
U.S. Appl. No. 10/837,379, filed Apr. 30, 2004.
U.S. Appl. No. 10/966,764, filed May 12, 2005.
U.S. Appl. No. 11/039,192, filed Aug. 18, 2005.
U.S. Appl. No. 11/118,519, filed Apr. 29, 2005.
U.S. Appl. No. 11/303,462, filed Dec. 15, 2005.
U.S. Appl. No. 11/368,845, filed Mar. 6, 2006.
U.S. Appl. No. 11/371,118, filed Mar. 8, 2006.
U.S. Appl. No. 11/395,019, filed Mar. 31, 2006.
U.S. Appl. No. 11/455,392, filed Dec. 20, 2007.
U.S. Appl. No. 11/552,835, filed Apr. 24, 2008.
U.S. Appl. No. 11/565,917, filed Dec. 1, 2006.
U.S. Appl. No. 11/741,366, filed Sep. 27, 2007.
U.S. Appl. No. 11/859,627, filed Mar. 26, 2009.
U.S. Appl. No. 11/952,927, filed Dec. 7, 2007.
U.S. Appl. No. 11/952,938, filed Dec. 7, 2007.
U.S. Appl. No. 12/028,762, filed Feb. 8, 2008.
U.S. Appl. No. 12/028,763, filed Feb. 8, 2008.
U.S. Appl. No. 12/255,497, filed Oct. 21, 2008.
U.S. Appl. No. 12/259,153, filed Oct. 27, 2008.
U.S. Appl. No. 12/355,709, filed Jan. 16, 2009.
U.S. Appl. No. 12/411,250, filed Mar. 25, 2009.
U.S. Appl. No. 12/761,765, filed Apr. 16, 2010.
U.S. Appl. No. 13/011,467, filed Jan. 21, 2011.
U.S. Appl. No. 13/152,780, filed Jun. 3, 2011.
U.S. Appl. No. 13/466,752, filed May 8, 2012.
U.S. Appl. No. 13/466,804, filed May 8, 2012.
U.S. Appl. No. 13/511,548, filed May 23, 2012.
U.S. Appl. No. 60/567,423, filed Apr. 30, 2004.
U.S. Appl. No. 60/567339, filed Apr. 30, 2004.
U.S. Appl. No. 61/287,078, filed Dec. 16, 2009.
U.S. Appl. No. 61/297,660, filed Jan. 22, 2010.
U.S. Appl. No. 10/836,911, filed Apr. 30, 2004.
U.S. Appl. No. 11/552,630, filed Feb. 7, 2008.

United States Board of Appeals and Interferences decision on appeal in Ex parte Huang et al, Appeal No. 2009-013914, U.S. Appl. No. 10/340,237, mailed Sep. 21, 2010.

United States Board of Patent and Interferences decision on appeal in Ex parte Huang et al, Appeal No. 2010-006865, U.S. Appl. No. 10/836,880, mailed Sep. 28, 2010.

United States Board of Patent Appeals and Interferences decision on appeal in Ex parte Hughes et al, Appeal No. 2010-004999, U.S. Appl. No. 10/836,911, mailed Oct. 25, 2010.

United States Board of Patent Appeals and Interferenms on appeal in Ex parte Hughes et al, Appeal No. 2011-003859, U.S. Appl. No. 11/116,698, mailed Aug. 1, 2011.

United States Pharmacopeia, The National Formulary, USP23, 1995, 1790-1798, 18.

U.S. Appl. No. 11/118,519, filed Apr. 29, 2004.

Wadood, Azfar et al, Safety and Efficacy of a Dexamethasone Anterior Segment Delivery System in Patients After Phacoemulsification, Journal of Cataract and Refractive Surgery, Apr. 2004, 761-768, 30.

Watson, Peter et al, A Six-month, Randomized, Double-masked Study Comparing Latanoprost with Timolol in Open-Angle Glaucoma and Ocular Hypertension, Ophthalmology, 1996, 126-137, 103.

Wheeler, Larry et al, From the Lab to the Clinic: Activation of an Alpha-2 Agonist Pathway is Neuroprotective in Models of Retinal and Optic Nerve Injury, Eur. J. Ophthalmology, 1999, S17-S22, 9 (1).

Wheeler, Larry et al, Role of Alpha-2-Agonist in Neuroprotection, Sur Ophthalmol, 2003, S47-S51, 48(Suppl 1).

Wheeler, Larry, Experimental Study of Agents with Potential Neuroprotective Properties, Acta Ophthalmol Scand, 1999, 27-28, 77.

Wine, N.A. et al, The Ocular Uptake of Subconjunctivally Injected C14 Hydrocortisone, Am. J. Ophthalmol., 1964, 362-366, 58.

Wischke, Christian et al, Principles of Encapsulating Hydrophobic Drugs in PLA/PLGA Microparticles, International Journal of Pharmaceutics, 2008, 298-327, 364.

Woldemussie, Elizabeth et al, Neuoprotection Effects of Memantine in Different Retinal Injury Models of Glaucoma, J Glaucoma, 2002, 474-480, 11(6).

Woldemussie, Elizabeth, Neuroprotection of Retinal Ganglion Cells in Experimental Models of Glaucoma, Minerva Ophthalmol, 2000, 71-78, 42(2).

Woodward, David et al, AGN 192024 (LumiganR): A Synthetic Prostamide Analog that Lowers Primate Intraocular Pressure by Virtue of Its Inherent Pharmacological Activity, ARVO, 2002, 1 page (Abstract), 43.

(56) References Cited

OTHER PUBLICATIONS

Woodward, David et al, Eicosanoid Receptors: Pharmacology and Ocular Distribution, Exp Eye Res, Sep. 1996, S23-Abstract 2, 63(Suppl 1).
Woodward, David et al, The molecular biology and ocular distribution of prostanoid receptors, Surv Ophthalmol, Feb. 1997, S15-S21, 41(Suppl 2).
Woodward, David et al, The Pharmacology of Bimatoprost (Lumigan™), Surv Ophthalmol, 2001, S337-S345, Suppl 4.
Woodward, et al., "Fixed-Combination and Emerging Glaucoma Therapies", Expert Opinion on Emerging Drugs, 2007, 313-327, 12(2).
Zhou, Tianhong et al, Development of a Multiple-Drug Delivery Implant for Intraocular Management of Proliferative Vitreoretinopathy, Journal of Controlled Release, 1998, 281-295, 55.

\* cited by examiner

15β AGN 192024

5,6-trans AGN 192024 isomer

C1 Acid of AGN 192024

Triphenylphoshpine Oxide (TPPO)

15-Keto AGN 192024 (Formerly "Impurity A")

DL040 (non sterile)
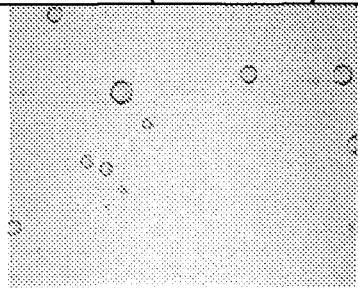
FIG. 5A
DL041 (non sterile)
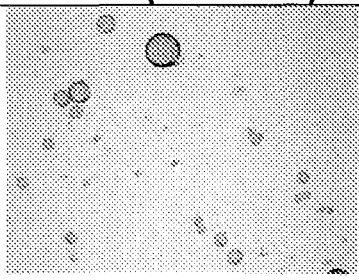
FIG. 5B
| DL042 (non sterile) | DL042 (gamma sterile) |
|---|---|
| 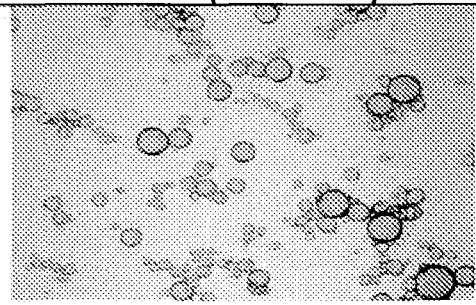 | 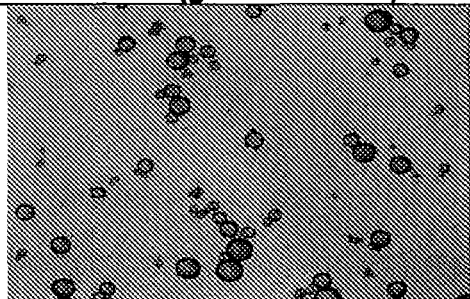 |
| FIG. 5C | FIG. 5D |
| DL043 (non sterile) | DL043 (gamma sterile) |
| 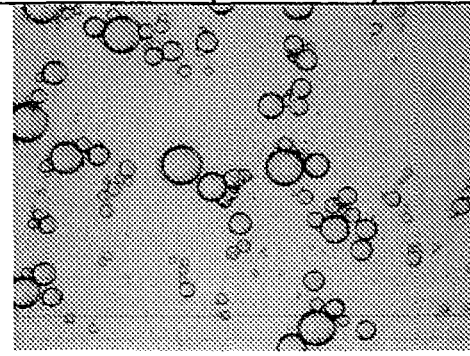 | 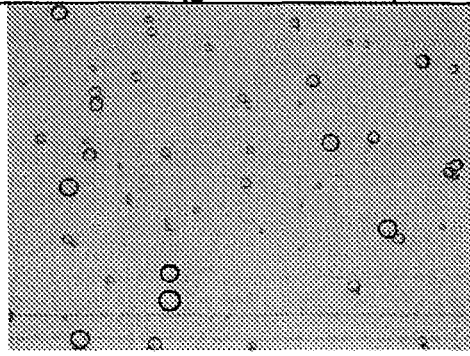 |
| FIG. 5E | FIG. 5F |

OIL-IN-WATER METHOD FOR MAKING POLYMERIC IMPLANTS CONTAINING A HYPOTENSIVE LIPID

CROSS-REFERENCE TO RELATED APPLICATIONS

This application is a continuation application of U.S. patent application Ser. No. 14/228,020 filed Mar. 27, 2014, which is a divisional application of U.S. patent application Ser. No. 11/371,118 filed Mar. 8, 2006 which is a continuation-in-part of U.S. patent application Ser. No. 11/368,845 filed Mar. 6, 2006, which is a continuation-in-part of U.S. application Ser. No. 11/303,462, filed Dec. 15, 2005 which is a continuation-in-part of application Ser. No. 10/837,260, filed Apr. 30, 2004, the entire contents of which prior applications are hereby incorporated by reference.

BACKGROUND

The present invention generally relates to methods for treating an eye of a patient, and more specifically to methods comprising subconjunctival administration microparticles to an eye that provide therapeutic agents, such as ophthalmically active cyclic lipid components, to an eye in which the microparticles are placed.

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupillary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical beta-adrenoreceptor antagonists have traditionally been the drugs of choice for treating glaucoma.

Prostaglandins were earlier regarded as potent ocular hypertensives; however, evidence accumulated in the last two decades shows that some prostaglandins are highly effective ocular hypotensive agents and are ideally suited for the long-term medical management of glaucoma. (See, for example, Starr, M. S. Exp. Eye Res. 1971, 11, pp. 170-177; Bito, L. Z. Biological Protection with Prostaglandins Cohen, M. M., ed., Boca Raton, Fla., CRC Press Inc., 1985, pp. 231-252; and Bito, L. Z., Applied Pharmacology in the Medical Treatment of Glaucomas Drance, S. M. and Neufeld, A. H. eds., New York, Grune & Stratton, 1984, pp. 477-505). Such prostaglandins include $PGF_{2\alpha}$, $PGF_{1\alpha}$, $PGE_2$, and certain lipid-soluble esters, such as $C_1$ to $C_5$ alkyl esters, e.g. 1-isopropyl ester, of such compounds.

In U.S. Pat. No. 4,599,353 certain prostaglandins, in particular $PGE_2$ and $PGF_{2\alpha}$ and the $C_1$ to $C_5$ alkyl esters of the latter compound, were reported to possess ocular hypotensive activity and were recommended for use in glaucoma management.

Although the precise mechanism is not yet known, recent experimental results indicate that the prostaglandin-induced reduction in intraocular pressure results from increased uveoscleral outflow [Nilsson et al., Invest. Ophthalmol. Vis. Sci. 28(suppl), 284 (1987)].

The isopropyl ester of $PGF_{2\alpha}$ has been shown to have significantly greater hypotensive potency than the parent compound, which was attributed to its more effective penetration through the cornea. In 1987, this compound was described as "the most potent ocular hypotensive agent ever reported." [See, for example, Bito, L. Z., Arch. Ophthalmol. 105, 1036 (1987), and Siebold et al., Prodrug 5, 3 (1989)].

Whereas prostaglandins appear to be devoid of significant intraocular side effects, ocular surface (conjunctival) hyperemia and foreign-body sensation have been consistently associated with the topical ocular use of such compounds, in particular $PGF_{2\alpha}$ and its prodrugs, e.g. its 1-isopropyl ester, in humans. The clinical potential of prostaglandins in the management of conditions associated with increased ocular pressure, e.g. glaucoma, is greatly limited by these side effects.

Certain prostaglandins and their analogs and derivatives, such as the $PGF_{2\alpha}$ derivative latanoprost, sold under the trademark Xalatan®, have been established as compounds useful in treating ocular hypertension and glaucoma. However, latanoprost, the first prostaglandin approved by the United States Food And Drug Administration for this indication, is a prostaglandin derivative possessing the undesirable side effect of producing an increase in brown pigment in the iris of 5-15% of human eyes. The change in color results from an increased number of melanosomes (pigment granules) within iridial melanocytes. See e.g., Watson et al., Ophthalmology 103:126 (1996). While it is still unclear whether this effect has additional and deleterious clinical ramifications, from a cosmetic standpoint alone such side effects are undesirable.

Certain phenyl and phenoxy mono, tri and tetra prostaglandins and their 1-esters are disclosed in European Patent Application 0,364,417 as useful in the treatment of glaucoma or ocular hypertension.

In a series of United States patent applications assigned to Allergan, Inc. prostaglandin esters with increased ocular hypotensive activity accompanied with no or substantially reduced side-effects are disclosed. U.S. Pat. application Ser. No. 386,835 (filed Jul. 27, 1989), relates to certain 11-acyl-prostaglandins, such as 11-pivaloyl, 11-acetyl, 11-isobutyryl, 11-valeryl, and 11-isovaleryl $PGF_{2\alpha}$. Intraocular pressure reducing 15-acyl prostaglandins are disclosed in U.S.

Ser. No. 357,394 (filed May 25, 1989). Similarly, 11,15-9, 15- and 9,11-diesters of prostaglandins, for example 11,15-dipivaloyl $PGF_{2\alpha}$ are known to have ocular hypotensive activity. See U.S. Ser. No. 385,645 filed Jul. 27, 1990, now U.S. Pat. Nos. 4,494,274; 584,370 which is a continuation of U.S. Ser. No. 386,312, and U.S. Ser. No. 585,284, now U.S. Pat. No. 5,034,413 which is a continuation of U.S. Ser. No. 386,834, where the parent applications were filed on Jul. 27, 1989.

Woodward et al U.S. Pat. Nos. 5,688,819 and 6,403,649 disclose certain cyclopentane heptanoic acid, 2-cycloalkyl or arylalkyl compounds as ocular hypotensives. These compounds, which can properly be characterized as hypotensive lipids, are effective in treating ocular hypertension.

As one example, the prostamide analog, bimatoprost, has been discovered to be effective in reducing intraocular pressure possibly by increasing the aqueous humour outflow of an eye (Woodward et al., AGN 192024 (Lumigan®): A Synthetic Prostamide Analog that Lowers Primate Intraocular Pressure by Virtue of Its Inherent Pharmacological Activity, ARVO 2002; (CD-ROM):POS; Chen et al., Lumigan®: A Novel Drug for Glaucoma Therapy, Optom In Pract, 3:95-102 (2002); Coleman et al., A 3-Month Randomized Controlled Trial of Bimatoprost (LUMIGAN) versus Combined Timolol and Dorzolamide (Cosopt) in Patients with Glaucoma or Ocular Hypertension, Ophthalmology 110(12): 2362-8 (2003); Brubaker, Mechanism of Action of Bimatoprost (Lumigan™), Surv Ophthalmol 45 (Suppl 4):S347-S351 (2001); and Woodward et al., The Pharmacology of Bimatoprost (Lumigan™), Surv Ophthalmol 45 (Suppl 4) S337-S345 (2001).

Bimatoprost is an analog (e.g., a structural derivative) of a naturally occurring prostamide. Bimatoprost's chemical name is (Z)-7-[(1R,2R,3R,5S)-3,5-Dihydroxy-2-[1E,3 S)-3-hydroxy-5-phenyl-1-pentenyl]cyclopentyl]-5-N-ethylheptenamide, and it has a molecular weight of 415.58. Its molecular formula is $C_{25}H_{37}NO_4$. Bimatoprost is available in a topical ophthalmic solution under the tradename Lumigan® (Allergan, Inc.). Each mL of the solution contains 0.3 mg of bimatoprost as the active agent, 0.05 mg of benzalkonium chloride (BAK) as a preservative, and sodium chloride, sodium phosphate, dibasic; citric acid; and purified water as inactive agents.

Biocompatible implants for placement in the eye have been disclosed in a number of patents, such as U.S. Pat. Nos. 4,521,210; 4,853,224; 4,997,652; 5,164,188; 5,443,505; 5,501,856; 5,766,242; 5,824,072; 5,869,079; 6,074,661; 6,331,313; 6,369,116; and 6,699,493.

Yamada et al. US Patent Publication 2006/0013859 discuss the subconjunctival injection of gels or liquids capable of forming gels in situ in which a sparingly soluble drug-containing component is contained, in order to form a depot for ocular drug delivery, including delivery of such drugs to the posterior segment of the eye.

It would be advantageous to provide methods using eye implantable drug delivery systems, such as microparticles that are capable of releasing a therapeutic agent, such as a cyclic lipid component, preferably at a sustained or controlled rate for extended periods of time and in amounts with few or no negative side effects. In those cases in which it may provide a possible alternative to topical drug delivery, such a system would automatically release the drug over a period of time, thus reducing concerns with daily patient compliance.

SUMMARY

The present invention provides new drug delivery methods for drug release, advantageously extended and/or sustained and/or controlled drug release, into an eye, for example, to achieve one or more desired therapeutic effects. The present methods employ drug delivery systems in the form of microparticles that are administered subconjunctivally to an eye. The present methods advantageously provide for extended release times of one or more therapeutic agents, such as one or more ophthalmically active cyclic lipid components. Thus, the patient in whose eye the microparticles have been placed receives a therapeutic amount of an agent or agents for a relatively long or extended time period without requiring additional administrations of the agent or agents. For example, the patient has a therapeutically active agent available for treatment of the eye over a relatively long period of time, for example, on the order of at least about one week, such as between about two and about six months after administering the microparticles. Such extended release times facilitate obtaining successful treatment results. In addition, administering such microparticles subconjunctivally preferably reduces the occurrence and/or severity of at least one side effect, for example, hyperemia, relative to administering an identical amount of the cyclic lipid component to the eye in the form of a topical composition. Further, subconjunctival administration of microparticles comprising cyclic lipid components has unexpectedly been found to be highly effective in providing such cyclic lipid components to the retina of the eye. In Laedwif M. S. et al., *PROSTAGLANDINS LEUKOT. ESSENT. FATTY ACIDS* 72:251-6 (Apr. 2005), hereby incorporated by reference herein, a study showed infusion treatment of patients suffering from age-related macular degeneration (ARMD), particularly dry ARMD, with a cyclic lipid (prostaglandin E1) results in an improvement in visual acuity in 8/11 patients two months after the end of the infusion period. As the subconjunctival administration of microspheres containing a cyclic lipid component results in particularly effective delivery of such agents to the retina, the present invention would provide a particularly advantageous method of delivering the drug to ocular tissue without the possibility of side effects which may occur in the systemic administration of certain such cyclic lipids.

Microparticles in accordance with the disclosure herein comprise a therapeutic component and a drug release sustaining component associated with the therapeutic component. In accordance with the present invention, the therapeutic component comprises, consists essentially of, or consists of, a cyclic lipid component, such as, without limitation, a prostaglandin, prostaglandin analog, prostaglandin derivative, prostamide, prostamide analog, and a prostamide derivative that is effective in providing an ophthalmic therapeutic effect, such as, without limitation, reducing or maintaining a reduced intraocular pressure in a hypertensive eye, or providing to the retina of an eye an effective amount of a cyclic lipid component having neuroprotective activities. The microparticles are associated with the therapeutic component to sustain release of an amount of the cyclic lipid component into an eye in which the microparticles are placed. The cyclic lipid component is released into the eye for an extended period of time after the microparticles are administered subconjunctivally and is effective in treating or reducing at least one symptom of an ocular condition of an eye. Advantageously, the present microparticles may be effective in relieving a hypertensive eye by reducing the intraocular pressure of the eye or maintaining the intraocular pressure at a reduced level without substantial amounts of ocular hyperemia. Alternatively, the present microparticles may be effective in relieving disorders of the posterior segment of the eye, particularly, a retinal condition such as exudative or non-exudative age-related macular degeneration, by delivering cyclic lipid components via the sclera to the tissues of the posterior segment, in particular, the retina.

Embodiments of the present cyclic lipid-containing microparticles can be understood from the following description and claims.

In one embodiment, the microparticles comprise a cyclic lipid component and a biodegradable polymer matrix. The cyclic lipid component is associated with a biodegradable polymer matrix that releases drug at a rate effective to sustain release of an amount of the cyclic lipid component from the microparticles effective to treat an ocular condition. The microparticles are biodegradable or bioerodible and provide a sustained release of the cyclic lipid component to either or both the anterior and posterior segments of the eye for extended periods of time, such as for more than one week, for example for about three months or more and up to about six months or more.

The biodegradable polymer component of the foregoing microparticles may be a mixture of biodegradable polymers, wherein at least one of the biodegradable polymers is a polylactic acid polymer having a molecular weight less than 64 kiloDaltons (kD). Additionally or alternatively, the foregoing microparticles may comprise a first biodegradable polymer of a polylactic acid, and a different second biodegradable polymer of a polylactic acid. Furthermore, the foregoing microparticles may comprise a mixture of different biodegradable polymers, each biodegradable polymer having an inherent viscosity in a range of about 0.2 deciliters/gram (dl/g) to about 1.0 dl/g.

The cyclic lipid component of the implants disclosed herein may include a therapeutic component comprising a prostaglandin, prostaglandin analog, prostaglandin derivative, prostamide, prostamide analog, or a prostamide derivative, that is effective in treating ocular conditions. One example of a suitable prostamide derivative is bimatoprost. Other examples of cyclic lipid components of the present invention include, without limitation, latanoprost, travoprost and unoprostone and salts derivatives, and analogs of these. In addition, the therapeutic component of the present microspheres may include one or more additional and different therapeutic agents that may be effective in treating an ocular condition.

A method of making the present microspheres involves combining or mixing the cyclic lipid component with a biodegradable polymer or polymers. The mixture may then be extruded or compressed to form a single composition. The single composition may then be processed to form microspheres suitable for placement subconjunctivally.

A method of making the present microspheres may also include using an oil-in-oil emulsion process to form the microspheres. Such methods may be particularly useful in forming microparticles, nanoparticles and the like. Thus, an embodiment of the present invention relates to methods of making microparticles using an oil-in-oil emulsion process and microparticles so produced, as described herein.

The microspheres, which may include a population of microparticles or nanoparticles, may be placed in an ocular region such as, without limitation, subconjunctivally, to treat a variety of ocular conditions of the anterior or posterior segment. For example, the microspheres may be effective in delivering a therapeutic component comprising a cyclic lipid to tissues of the anterior segment, thereby reducing ocular hypertension, and thus may be effective in reducing at least one symptom of an ocular condition associated with an increased intraocular pressure. Alternatively, subconjunctival administration if the microspheres of the present invention are very effective at delivering the therapeutic component to the retina and other tissues of the posterior segment for the treatment of neurodegenerative conditions such as age related macular degeneration (ARMD), such as "wet" or "dry" ARMD.

Kits in accordance with the present invention may comprise one or more of the present microspheres, and instructions for using the microspheres. For example, the instructions may explain how to administer the microspheres to a patient, and types of conditions that may be treated with the microspheres.

The present invention also encompasses the use of the present microspheres in treating a patient, such as in treating one or more of the conditions or diseases set forth herein, as well as medicaments, which are oil-in-oil emulsified microparticles, for treating an ocular condition of a patient. The invention also encompasses the use of a cyclic lipid component and a polymeric component, as described herein, in the manufacture of a medicament for treating a patient.

As an alternative to subconjunctival injection, the drug containing microspheres disclosed herein can be placed onto the surface of the eye by injection through a hollow dome sutured onto the eye, as set forth for example in U.S. patent application Ser. No. 2005/113806A1 and in international patent application WO 03/020172A1, to thereby prevent or reduce the leaching or wash out of the drug from the site of its ocular administration.

Additional aspects and advantages of the present invention are set forth in the following description and claims, particularly when considered in conjunction with the accompanying drawings.

BRIEF DESCRIPTION OF THE DRAWINGS

FIG. 5A is a photograph of one batch of sterile microspheres.
FIG. 5B is a photograph of a different batch of sterile microspheres other than the batch of FIG. 5A.

FIG. 5C is a photograph of non-sterile microspheres.

FIG. 5D is a photograph of sterile microspheres.

FIG. 5E is a photograph of a non-sterile batch of microspheres.

FIG. 5F is a photograph of sterile microspheres.

DESCRIPTION

Figure 1:
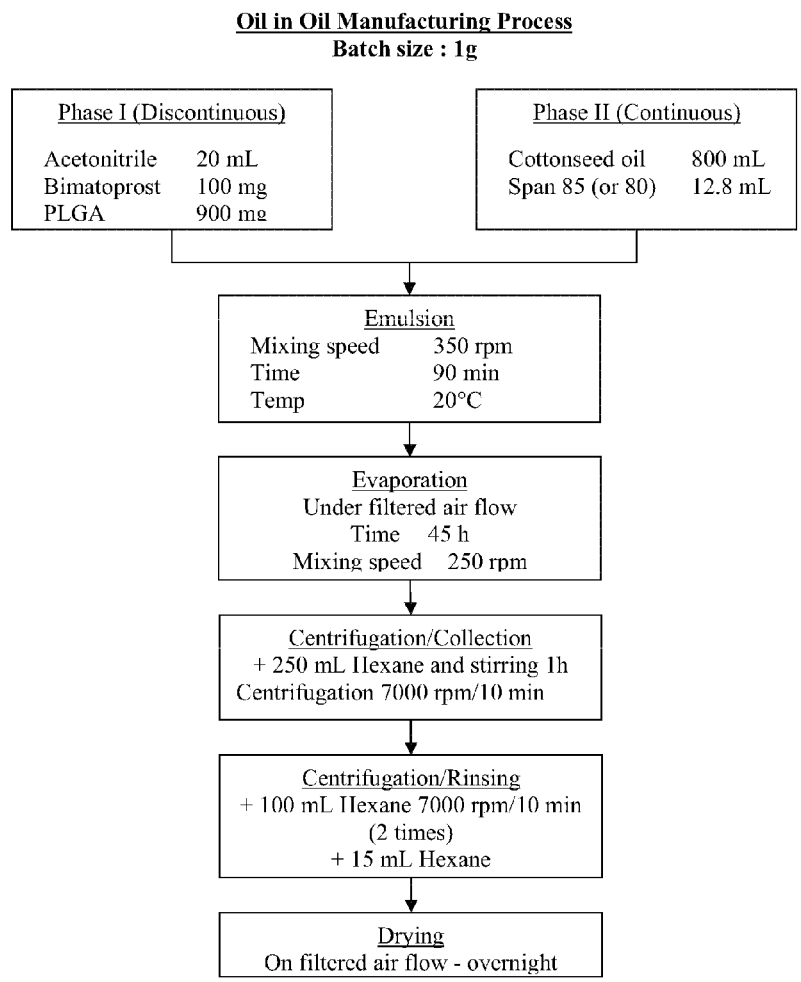
FIG. 1 is flow chart of a method of making microspheres.

As described herein, controlled and sustained administration of a therapeutic agent through the subconjunctival administration of one or more microparticles, may improve treatment of undesirable ocular conditions of the anterior or posterior segment. The microparticles comprise a pharmaceutically acceptable polymeric composition and are formulated to release one or more pharmaceutically active agents, such as a cyclic lipid, or other intraocular pressure lowering or neuroprotective agent, over an extended period of time. The microspheres are effective to provide a therapeutically effective dosage of the agent or agents to a region of the eye to treat or prevent one or more undesirable ocular conditions. Thus, with a single administration, cyclic lipids will be made available at the site where they are needed and will be maintained for an extended period of time, rather than subjecting the patient to repeated injections or repeated administration of topical drops.

The microparticles of the present invention comprise a therapeutic component and a drug release-sustaining component associated with the therapeutic component. In accordance with the present invention, the therapeutic component comprises, consists essentially of, or consists of, a cyclic lipid component. The drug release sustaining component is associated with the therapeutic component to sustain release of an effective amount of the cyclic lipid component into an eye in which the microparticles are placed. The amount of the cyclic lipid component is released into the eye for a period of time greater than about one week after the microparticles are placed in the eye, and is effective in treating or reducing a symptom of an ocular condition, such as ocular hypertension of retinal degeneration.

Definitions

For the purposes of this description, we use the following terms as defined in this section, unless the context of the word indicates a different meaning.

As used herein, a "microsphere" or "microparticle" are interchangeably used to refer to a device or element that is structured, sized, or otherwise configured to be administered subconjunctivally. It will be understood that the term microspheres or microparticles includes particles, micro or nanospheres, small fragments, microparticles, nanoparticles, fine powders and the like comprising a biocompatible matrix encapsulating or incorporating a therapeutic component. Microspheres are generally biocompatible with physiological conditions of an eye and do not cause adverse side effects. Microspheres administered subconjunctivally may be used safely without disrupting vision of the eye. Microspheres have a maximum dimension, such as diameter or length, less than 1 mm. For example, microparticles can have a maximum dimension less than about 500 μm. Microparticles may also have a maximum dimension no greater than about 200 μm, or may have a maximum dimension from about 30 μm to about 50 μm, among other sizes.

As used herein, a "therapeutic component" refers to that portion of a microsphere other than the polymer matrix comprising one or more therapeutic agents or substances used to treat a medical condition of the eye. The therapeutic component may be a discrete region of a microsphere, or it may be homogenously distributed throughout the microsphere. The therapeutic agents of the therapeutic component comprise at least one cyclic lipid and are typically ophthalmically acceptable, and are provided in a form that does not cause significant adverse reactions when the microsphere is placed in an eye.

As used herein, a "cyclic lipid component" refers to a portion of an intraocular implant that comprises one or more cyclic lipids having ocular therapeutic activity, including, without limitation, a prostaglandin, prostaglandin analog, prostaglandin derivative, prostamide, prostamide analog, and a prostamide derivative that is effective in providing an ophthalmic therapeutic effect, such as, without limitation, reducing or maintaining a reduced intraocular pressure in a hypertensive eye, or providing to the retina of an eye an effective amount of a cyclic lipid component having neuroprotective activities. Cyclic lipids having anti-glaucoma activity can be identified by applying the cyclic lipid to an eye with increased intraocular pressure, and evaluating whether the intraocular pressure decreases after the application. Cyclic lipids having neuroprotective activity may be identified by, for example, intravitreal administration of the cyclic lipid to an eye having a neurodegenerative disorder such as ARMD, and evaluating whether the neurodegeneration is slowed or halted, or whether visual acuity has increased.

As used herein, a "drug release sustaining component" refers to a portion of the microsphere that is effective to provide a sustained release of the therapeutic agents from the microsphere. A drug release sustaining component may be a biodegradable polymer matrix, or it may be a coating covering a core region of the microsphere that comprises a therapeutic component.

As used herein, "associated with" means mixed with, dispersed within, coupled to, covering, or surrounding.

As used herein, an "ocular region" or "ocular site" refers generally to any area of the eyeball, including the anterior and posterior segment of the eye, and which generally includes, but is not limited to, any functional (e.g., for vision) or structural tissues found in the eyeball, or tissues or cellular layers that partly or completely line the interior or exterior of the eyeball. Specific examples of areas of the eyeball in an ocular region include the anterior chamber, the posterior chamber, the vitreous cavity, the choroid, the suprachoroidal space, the conjunctiva, the subconjunctival space, the episcleral space, the intracorneal space, the epicorneal space, the sclera, the pars plana, surgically-induced avascular regions, the macula, and the retina.

As used herein, an "ocular condition" is a disease, ailment or condition which affects or involves the eye or one of the parts or regions of the eye. Broadly speaking the eye includes the eyeball and the tissues and fluids which constitute the eyeball, the periocular muscles (such as the oblique and rectus muscles) and the portion of the optic nerve which is within or adjacent to the eyeball.

An anterior ocular condition is a disease, ailment or condition which affects or which involves an anterior (i.e. front of the eye) ocular region or site, such as a periocular muscle, an eye lid or an eye ball tissue or fluid which is located anterior to the posterior wall of the lens capsule or ciliary muscles. Thus, an anterior ocular condition primarily affects or involves the conjunctiva, the cornea, the anterior chamber, the iris, the posterior chamber (behind the retina but in front of the posterior wall of the lens capsule), the lens or the lens capsule and blood vessels and nerve which vascularize or innervate an anterior ocular region or site.

Thus, an anterior ocular condition can include a disease, ailment or condition, such as for example, aphakia; pseudophakia; astigmatism; blepharospasm; cataract; conjunctival diseases; conjunctivitis; corneal diseases; corneal ulcer; dry eye syndromes; eyelid diseases; lacrimal apparatus diseases; lacrimal duct obstruction; myopia; presbyopia; pupil disorders; refractive disorders and strabismus. Glaucoma can also be considered to be an anterior ocular condition because a clinical goal of glaucoma treatment can be to reduce a hypertension of aqueous fluid in the anterior chamber of the eye (i.e. reduce intraocular pressure).

A posterior ocular condition is a disease, ailment or condition which primarily affects or involves a posterior ocular region or site such as choroid or sclera (in a position posterior to a plane through the posterior wall of the lens capsule), vitreous, vitreous chamber, retina, optic nerve (i.e. the optic disc), and blood vessels and nerves which vascularize or innervate a posterior ocular region or site.

Thus, a posterior ocular condition can include a disease, ailment or condition, such as for example, acute macular neuroretinopathy; Behcet's disease; choroidal neovascularization; diabetic uveitis; histoplasmosis; infections, such as fungal or viral-caused infections; macular degeneration, such as acute macular degeneration, non-exudative age related macular degeneration and exudative age related macular degeneration; edema, such as macular edema, cystoid macular edema and diabetic macular edema; multifocal choroiditis; ocular trauma which affects a posterior ocular site or location; ocular tumors; retinal disorders, such as central retinal vein occlusion, diabetic retinopathy (including proliferative diabetic retinopathy), proliferative vitreoretinopathy (PVR), retinal arterial occlusive disease, retinal detachment, uveitic retinal disease; sympathetic; ophthalmia; Vogt Koyanagi-Harada (VKH) syndrome; uveal diffusion; a posterior ocular condition caused by or influenced by an ocular laser treatment; posterior ocular conditions caused by or influenced by a photodynamic therapy, photocoagulation, radiation retinopathy, epiretinal membrane disorders, branch retinal vein occlusion, anterior ischemic optic neuropathy, non-retinopathy diabetic retinal dysfunction, retinitis pigmentosa, and glaucoma. Glaucoma can be considered a posterior ocular condition because the therapeutic goal is to prevent the loss of or reduce the occurrence of loss of vision due to damage to or loss of retinal cells or optic nerve cells (i.e. neuroprotection).

The term "biodegradable polymer" refers to a polymer or polymers which degrade in vivo, and wherein erosion of the polymer or polymers over time occurs concurrent with or subsequent to release of the therapeutic agent. Specifically, hydrogels such as methylcellulose which act to release drug through polymer swelling are specifically excluded from the term "biodegradable polymer". The terms "biodegradable" and "bioerodible" are equivalent and are used interchangeably herein. A biodegradable polymer may be a homopolymer, a copolymer, or a polymer comprising more than two different polymeric units.

The term "treat", "treating", or "treatment" as used herein, refers to reduction or resolution or prevention of an ocular condition, ocular injury or damage, or to promote healing of injured or damaged ocular tissue. A treatment is usually effective to reduce at least one symptom of an ocular condition, ocular injury or damage.

The term "therapeutically effective amount" as used herein, refers to the level or amount of agent needed to treat an ocular condition, or reduce or prevent ocular injury or damage without causing significant negative or adverse side effects to the eye or a region of the eye. In view of the above, a therapeutically effective amount of a therapeutic agent, such as a cyclic lipid, is an amount that is effective in reducing at least one symptom of an ocular condition.

Microspheres have been developed which can release drug loads over various time periods. These microspheres, which when inserted into the subconjunctival space of an eye provide therapeutic levels of a cyclic lipid for extended periods of time (e.g., for about 1 week or more). The disclosed microspheres are effective in treating ocular conditions, such as ocular conditions associated with elevated intraocular pressure, and more specifically in reducing at least one symptom of glaucoma.

Methods for producing microspheres have also been developed. For example, the present invention encompasses therapeutic polymeric microparticles and methods of making and using such microparticles. As disclosed herein, the microparticles may be oil-in-oil emulsified microparticles.

In one embodiment of the present invention, a microsphere comprises a biodegradable polymer matrix. The biodegradable polymer matrix is one type of a drug release sustaining component. The biodegradable polymer matrix is effective in forming a biodegradable microsphere. The biodegradable microsphere comprises a cyclic lipid component associated with the biodegradable polymer matrix. The matrix degrades at a rate effective to sustain release of an amount of the cyclic lipid component for a time greater than about one week from the time in which the microsphere is placed in ocular region or ocular site, such as the subconjunctival space of an eye.

The cyclic lipid component of the microsphere may include one or more types of prostaglandin, prostaglandin analog, prostaglandin derivative, prostamide, prostamide analog, and a prostamide derivative, and any salts thereof, and mixtures thereof. In certain microspheres, the cyclic lipid component may comprise a compound having the following formula (VI)

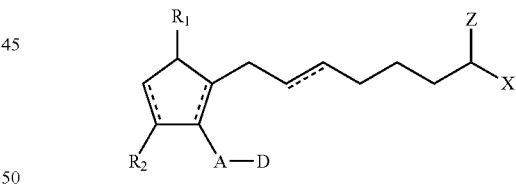

wherein the dashed bonds represent a single or double bonds which can be in the cis or trans configuration, A is an alkylene or alkenylene radical having from two to six carbon atoms, which radical may be interrupted by one or more oxide radicals and substituted with one or more hydroxy, oxo, alkoxy or alkylcarboxyl groups wherein said alkyl radical comprises from one to six carbon atoms; D is a branched or unbranched alkyl or heteroalkyl radical of from two to 10 carbon atoms, a cycloalkyl radical having from three to seven carbon atoms, or an aryl radical, selected from the group consisting of hydrocarbyl aryl and heteroaryl radicals having from four to ten carbon atoms wherein the heteroatom is selected from the group consisting of nitrogen, oxygen and sulfur atoms; X is a radical selected from the group consisting of hydrogen, a lower alkyl radical having from one to six carbon atoms, $R^5$—C(=O)— or $R^5$—O—

C(=O)-wherein $R^5$ is a lower alkyl radical having from one to six carbon atoms; Z is =O or represents 2 hydrogen radicals; one of $R_1$ and $R^2$ is =O, —OH or a —O—C(=O)—$R^6$ group, and the other one is —OH or —O—C(=O)—$R^6$, or $R^1$ is =O and $R^2$ is H, wherein $R^6$ is a saturated or unsaturated acyclic hydrocarbon group having from 1 to about 20 carbon atoms, or —(CH$_2$)—$R^7$ wherein m is 0-10, and $R^7$ is cycloalkyl radical, having from three to seven carbon atoms, or a hydrocarbyl aryl or heteroaryl radical, as defined above, or a pharmaceutically acceptable salt thereof.

Pharmaceutically acceptable acid addition salts of certain of the cyclic lipids of the invention are those formed from acids which form non-toxic addition salts containing pharmaceutically acceptable anions, such as the hydrochloride, hydrobromide, hydroiodide, sulfate, or bisulfate, phosphate or acid phosphate, acetate, maleate, fumarate, oxalate, lactate, tartrate, citrate, gluconate, saccharate and p-toluene sulphonate salts.

In further embodiments, the cyclic lipid component comprises a compound having the following formula (VII)

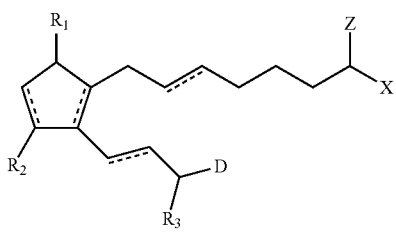

wherein the radicals are as defined for Formula VI.

In another embodiment, the cyclic lipids of the present invention may comprise a compound having the following formula (VII)

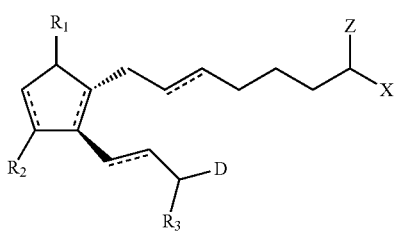

wherein hatched lines indicate the α configuration and the solid triangles comprise the β configuration and the radicals are as defined for Formula VI.

In a further embodiment, the cyclic lipid component comprises a compound having the following formula (VIII)

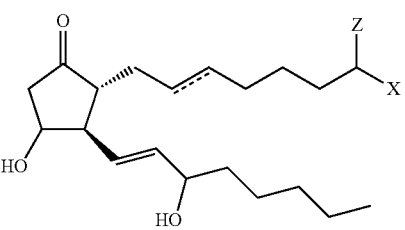

wherein the radicals are as defined for Formula VI.

In a further embodiment, the cyclic lipid component comprises a compound having the following formula (IX)

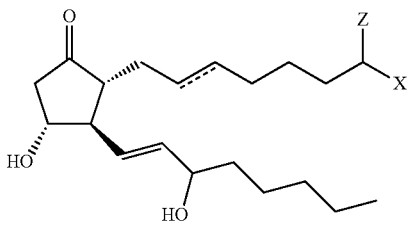

wherein X is as defined for Formula VI.

In a further embodiment, the cyclic lipid component comprises a compound having the following formula (X)

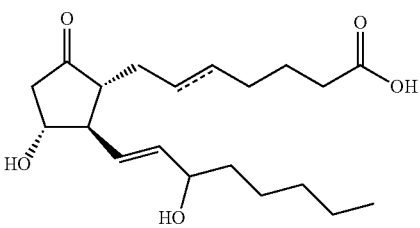

In particular, the cyclic lipid component may comprise prostaglandin E1 or prostaglandin E2, or salts, esters or mixtures thereof. It will be understood that the cyclic lipids used in the present invention include, where appropriate, salts or esters of any compound disclosed herein.

In another embodiment, the cyclic lipid component of the present invention may comprise a compound having the formula (I)

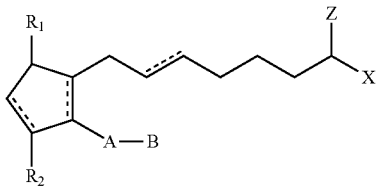

wherein the dashed bonds represent a single or double bond which can be in the cis or trans configuration, A is an alkylene or alkenylene radical having from two to six carbon atoms, which radical may be interrupted by one or more oxide radicals and substituted with one or more hydroxy, oxo, alkyloxy or alkylcarboxy groups wherein said alkyl radical comprises from one to six carbon atoms; B is a cycloalkyl radical having from three to seven carbon atoms, or an aryl radical, selected from the group consisting of hydrocarbyl aryl and heteroaryl radicals having from four to ten carbon atoms wherein the heteroatom is selected from the group consisting of nitrogen, oxygen and sulfur atoms; X is a radical selected from the group consisting of —$OR^4$ and —$N(R^4)_2$ wherein $R^4$ is selected from the group consisting of hydrogen, a lower alkyl radical having from one to six carbon atoms,

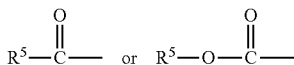

wherein $R^5$ is a lower alkyl radical having from one to six carbon atoms; Z is =O or represents 2 hydrogen radicals; one of $R_1$ and $R_2$ is =O, —OH or a —O(CO)$R_6$ group, and the other one is —OH or —O(CO)$R_6$, or $R_1$ is =O and $R_2$ is H, wherein $R_6$ is a saturated or unsaturated acyclic hydrocarbon group having from 1 to about 20 carbon atoms, or —(CH$_2$)$_m$R$_7$ wherein m is 0 or an integer of from 1 to 10, and $R_7$ is cycloalkyl radical, having from three to seven carbon atoms, or a hydrocarbyl aryl or heteroaryl radical, as defined above, or a pharmaceutically-acceptable salt thereof, provided, however, that when B is not substituted with a pendant heteroatom-containing radical, and Z is =O, then X is not —OR$^4$.

Pharmaceutically acceptable acid addition salts of certain of the compounds of the invention are those formed from acids which form non-toxic addition salts containing pharmaceutically acceptable anions, such as the hydrochloride, hydrobromide, hydroiodide, sulfate, or bisulfate, phosphate or acid phosphate, acetate, maleate, fumarate, oxalate, lactate, tartrate, citrate, gluconate, saccharate and p-toluene sulphonate salts.

In more specific implants, the compound of the prostamide component has the following formula (II)

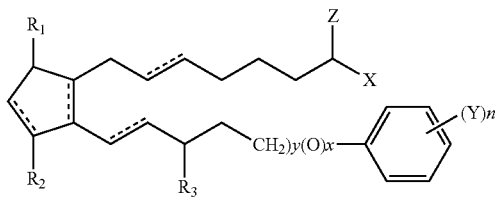

wherein y is 0 or 1, x is 0 or 1 and x+y are not both 1, Y is a radical selected from the group consisting of alkyl, halo, nitro, amino, thiol, hydroxy, alkyloxy, alkylcarboxy and halo substituted alkyl, wherein said alkyl radical comprises from one to six carbon atoms, n is 0 or an integer of from 1 to 3 and $R_3$ is =O, —OH or —O(CO)$R_6$.

In additional implants, the compound of the prostamide component has the following formula (III)

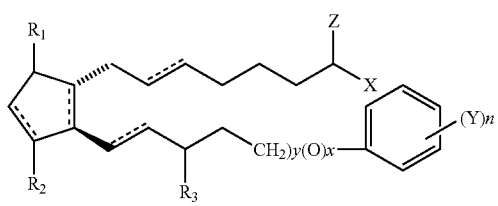

wherein hatched lines indicate the α configuration and solid triangles indicate the β configuration.

In certain implants, the compound of the prostamide component has the following formula (IV)

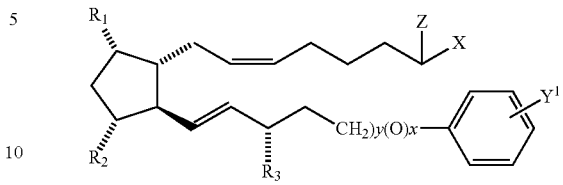

wherein $Y^1$ is Cl or trifluoromethyl, such as the compound having the following formula (V)

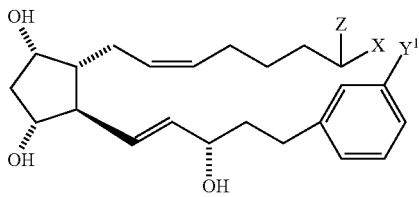

and the 9- and/or 11- and/or 15 esters thereof.

In another embodiment, the compounds used in conjunction with the resent invention include a) cyclopentane heptenol-5-cis-2-(3α-hydroxy-5-phenyl-1-trans-pentenyl)-3,5-dihydroxy, [1α, 2β, 3α, 5α];
b) cyclopentane heptenamide-5-cis-2-(3α-hydroxy-5-phenyl-1-trans-pentenyl)-3,5-dihydroxy, [1α, 2β, 3α, 5α];
c) cyclopentane N,N-dimethylheptenamide-5-cis-2-(3α-hydroxy-5-phenyl-1-trans-pentenyl)-3,5-dihydroxy, [1α, 2β, 3α, 5α];
d) cyclopentane heptenyl methoxide-5-cis-2-(3α-hydroxy-5-phenyl-1-trans-pentenyl)-3,5-dihydroxy, [1α, 2β, 3α, 5α];
e) cyclopentane heptenyl ethoxide-5-cis-2-(3α-hydroxy-4-meta-chloro-phenoxy-1-trans-1-butenyl)-3,5-dihydroxy, [1α, 2β, 3α, 5α];
f) cyclopentane heptenylamide-5-cis-2-(3α-hydroxy-4-meta-chloro-phenoxy-1-trans-butenyl)-3,5-dihydroxy, [1α, 2β, 3α, 5α];
g) cyclopentane heptenylamide-5-cis-2-(3α-hydroxy-4-meta-trifluoromethyl-phenoxy-1-trans-butenyl)-3,5-dihydroxy, [1α, 2β, 3α, 5α];
h) cyclopentane N-isopropyl hepteneamide-5-cis-2-(3α-hydroxy-5-phenyl-1-trans-pentenyl)-3,5-dihydroxy, [1α, 2β, 3α, 5α];
i) cyclopentane N-ethyl heptenamide-5-cis-2-(3α-hydroxy-5-phenyl-1-trans-pentenyl)-3,5-dihydroxy, [1α, 2β, 3α, 5α];
j) cyclopentane N-methyl heptenamide-5-cis-2-(3α-hydroxy-5-phenyl-1-trans-pentenyl)-3,5-dihydroxy, [1α, 2β, 3α, 5α];
k) cyclopentane heptenol-5-cis-2-(3α-hydroxy-4-meta-chlorophenoxy-1-trans-butenyl)-3,5-dihydroxy, [1α, 2β, 3α, 5α];
l) cyclopentane heptenamide-5-cis-2-(3α-hydroxy-4-meta-chlorophenoxy-1-trans-butenyl)-3,5-dihydroxy, [1α, 2β, 3α, 5α], and
m) cyclopentane heptenol-5-cis-2-(3α-hydroxy-5-phenyl-pentyl)3,5-dihydroxy, [1α, 2β, 3α, 5α].

The prostamide having a name cyclopentane N-ethyl heptenamide-5-cis-2-cis-2-(3α-hydroxy-5-phenyl-1-trans-pentenyl)-3,5-dihydroxy, [1α,2β,3α,5α], and derivatives, analogs, and/or esters thereof, is particularly preferred in this aspect of the invention. This compound is also known as bimatoprost and is publicly available in a topical ophthalmic solution under the tradename, Lumigan® (Allergan, Inc., CA).

Thus, the microparticles may comprise a therapeutic component which comprises, consists essentially of, or consists of bimatoprost, a salt thereof, or mixtures thereof.

The cyclic lipid component may be in a liquid, derivatized, particulate, or powder form and it may be entrapped by the biodegradable polymer matrix. Usually, cyclic lipid particles will have an effective average size less than about 3000 nanometers. In certain implants, the particles may have an effective average particle size about an order of magnitude smaller than 3000 nanometers. For example, the particles may have an effective average particle size of less than about 500 nanometers. In additional implants, the particles may have an effective average particle size of less than about 400 nanometers, and in still further embodiments, a size less than about 200 nanometers.

The cyclic lipid component of the microspheres is preferably from about 10% to 90% by weight of the microspheres. More preferably, the cyclic lipid component is from about 20% to about 80% by weight of the microspheres. In a preferred embodiment, the cyclic lipid component comprises about 20% by weight of the microsphere (e.g., 15%-25%). In another embodiment, the cyclic lipid component comprises about 50% by weight of the microspheres.

Suitable polymeric materials or compositions for use in the microspheres include those materials which are compatible, that is biocompatible, with the eye so as to cause no substantial interference with the functioning or physiology of the eye. Such materials preferably are at least partially and more preferably substantially completely biodegradable or bioerodible.

Examples of useful polymeric materials include, without limitation, such materials derived from and/or including organic esters and organic ethers, which when degraded result in physiologically acceptable degradation products, including the monomers. Also, polymeric materials derived from and/or including, anhydrides, amides, orthoesters and the like, by themselves or in combination with other monomers, may also find use. The polymeric materials may be addition or condensation polymers, advantageously condensation polymers. The polymeric materials may be cross-linked or non-cross-linked, for example not more than lightly cross-linked, such as less than about 5%, or less than about 1% of the polymeric material being cross-linked. For the most part, besides carbon and hydrogen, the polymers will include at least one of oxygen and nitrogen, advantageously oxygen. The oxygen may be present as oxy, e.g. hydroxy or ether, carbonyl, e.g. non-oxo-carbonyl, such as carboxylic acid ester, and the like. The nitrogen may be present as amide, cyano and amino. The polymers set forth in Heller, Biodegradable Polymers in Controlled Drug Delivery, In: CRC Critical Reviews in Therapeutic Drug Carrier Systems, Vol. 1, CRC Press, Boca Raton, Fla. 1987, pp 39-90, which describes encapsulation for controlled drug delivery, may find use in the present microspheres.

Of additional interest are polymers of hydroxyaliphatic carboxylic acids, either homopolymers or copolymers, and polysaccharides. Polyesters of interest include polymers of D-lactic acid, L-lactic acid, racemic lactic acid, glycolic acid, polycaprolactone, and combinations thereof. Generally, by employing the L-lactate or D-lactate, a slowly eroding polymer or polymeric material is achieved, while erosion is substantially enhanced with the lactate racemate.

Among the useful polysaccharides are, without limitation, calcium alginate, and functionalized celluloses, particularly carboxymethylcellulose esters characterized by being water insoluble, a molecular weight of about 5 kD to 500 kD, for example.

Other polymers of interest include, without limitation, polyvinyl alcohol, polyesters, polyethers and combinations thereof which are biocompatible and may be biodegradable and/or bioerodible.

Some preferred characteristics of the polymers or polymeric materials for use in the present invention may include biocompatibility, compatibility with the therapeutic component, ease of use of the polymer in making the drug delivery systems of the present invention, a half-life in the physiological environment of at least about 6 hours, preferably greater than about one day, and water insolubility.

The biodegradable polymeric materials which are included to form the matrix are desirably subject to enzymatic or hydrolytic instability. Water soluble polymers may be cross-linked with hydrolytic or biodegradable unstable cross-links to provide useful water insoluble polymers. The degree of stability can be varied widely, depending upon the choice of monomer, whether a homopolymer or copolymer is employed, employing mixtures of polymers, and whether the polymer includes terminal acid groups.

Equally important to controlling the biodegradation of the polymer and hence the extended release profile of the implant is the relative average molecular weight of the polymeric composition employed in the microspheres. Different molecular weights of the same or different polymeric compositions may be included in the microspheres to modulate the release profile. In certain implants, the relative average molecular weight of the polymer will range from about 9 to about 64 kD, usually from about 10 to about 54 kD, and more usually from about 12 to about 45 kD.

In some microspheres, copolymers of glycolic acid and lactic acid are used, where the rate of biodegradation is controlled by the ratio of glycolic acid to lactic acid. The most rapidly degraded copolymer has roughly equal amounts of glycolic acid and lactic acid. Homopolymers, or copolymers having ratios other than equal, are more resistant to degradation. The ratio of glycolic acid to lactic acid will also affect the brittleness of the microspheres. The percentage of polylactic acid in the polylactic acid polyglycolic acid (PLGA) copolymer can be 0-1000, preferably about 15-85%, more preferably about 35-65%. In some implants, a 50/50 PLGA copolymer is used.

The biodegradable polymer matrix of the subconjunctival microspheres may comprise a mixture of two or more biodegradable polymers. For example, the microspheres may comprise a mixture of a first biodegradable polymer and a different second biodegradable polymer. One or more of the biodegradable polymers may have terminal acid groups.

Release of a drug from an erodible polymer is the consequence of several mechanisms or combinations of mechanisms. Some of these mechanisms include desorption from the microsphere's surface, dissolution, diffusion through porous channels of the hydrated polymer and erosion. Erosion can be bulk or surface or a combination of both. As discussed herein, the matrix of the microspheres may release drug at a rate effective to sustain release of an amount of the prostamide component for more than one week after implantation into an eye. In certain microspheres, therapeutic amounts of the cyclic lipid component are released for no more than about 30-35 days after administration to the subconjunctival space. For example, a microsphere may comprise bimatoprost, and the matrix of the microsphere degrades at a rate effective to sustain release of a therapeutically effective amount of bimatoprost for about one month after being placed under the conjunctiva. As another example, the microspheres may comprise bimatoprost, and the matrix releases drug at a rate effective to sustain release of a therapeutically effective amount of bimatoprost for more than forty days, such as for about six months.

One example of the biodegradable microsphere comprises an cyclic lipid component associated with a biodegradable polymer matrix, which comprises a mixture of different biodegradable polymers. At least one of the biodegradable polymers is a polylactide having a molecular weight of about 63.3 kD. A second biodegradable polymer is a polylactide having a molecular weight of about 14 kD. Such a mixture is effective in sustaining release of a therapeutically effective amount of the cyclic lipid component for a time period greater than about one month from the time the microspheres are placed administered under the conjunctiva.

Another example of a biodegradable microsphere comprises a cyclic lipid component associated with a biodegradable polymer matrix, which comprises a mixture of different biodegradable polymers, each biodegradable polymer having an inherent viscosity from about 0.16 dl/g to about 1.0 dl/g. For example, one of the biodegradable polymers may have an inherent viscosity of about 0.3 dl/g. A second biodegradable polymer may have an inherent viscosity of about 1.0 dl/g. Additional microspheres may comprise biodegradable polymers that have an inherent viscosity between about 0.2 dl/g and 0.5 dl/g. The inherent viscosities identified above may be determined in 0.1% chloroform at 25° C.

One particular microsphere formulation comprises bimatoprost associated with a combination of two different polylactide polymers. The bimatoprost is present in about 20% by weight of the microsphere. One polylactide polymer has a molecular weight of about 14 kD and an inherent viscosity of about 0.3 dl/g, and the other polylactide polymer has a molecular weight of about 63.3 kD and an inherent viscosity of about 1.0 dl/g. The two polylactide polymers are present in the microsphere in a 1:1 ratio. Such a microsphere may be effective in releasing the bimatoprost for more than two months.

The release of the cyclic lipid component from microspheres into the subconjunctival may include an initial burst of release followed by a gradual increase in the amount of the cyclic lipid component released, or the release may include an initial delay in release of the prostamide component followed by an increase in release. When the microspheres are substantially completely degraded, the percent of the cyclic lipid component that has been released is about one hundred. The microsphere disclosed herein do not completely release, or release about 100% of the cyclic lipid component, until after about one week of being placed in an eye.

It may be desirable to provide a relatively constant rate of release of the cyclic lipid component from the microspheres over the life of the implant. For example, it may be desirable for the cyclic lipid component to be released in amounts from about 0.01 µg to about 2 µg per day for the life of the microspheres. However, the release rate may change to either increase or decrease depending on the formulation of the biodegradable polymer matrix. In addition, the release profile of the prostamide component may include one or more linear portions and/or one or more non-linear portions. Preferably, the release rate is greater than zero once the microspheres has begun to degrade or erode.

The microspheres may be monolithic, i.e. having the active agent or agents homogenously distributed through the polymeric matrix, or encapsulated, where a reservoir of active agent is encapsulated by the polymeric matrix. Due to ease of manufacture, monolithic implants are usually preferred over encapsulated forms. However, the greater control afforded by the encapsulated microspheres may be of benefit in some circumstances, where the therapeutic level of the drug falls within a narrow window. In addition, the therapeutic component, including the cyclic lipid component, may be distributed in a non-homogenous pattern in the matrix. For example, the microspheres may include a portion that has a greater concentration of the cyclic lipid component relative to a second portion of the microspheres.

The microspheres disclosed herein may have a size of between about 5 µm and about 1 mm, or between about 10 µm and about 0.8 mm for administration with a needle. For needle-injected microspheres, the microsphere may have any appropriate dimensions so long as the longest dimension of the microsphere permits the microsphere to move through a needle. This is generally not a problem in the administration of microspheres. The subconjunctival space in humans is able to accommodate relatively large volumes of microspheres, for example, about 100 µl, or about 150 µl, or about 50-200 µl or more.

The total weight of microsphere in a single dosage an optimal amount, depending on the volume of the subconjunctival space and the activity or solubility of the active agent. Most often, the dose is usually about 10 mg to about 500 mg of microspheres per dose. For example, a single subconjunctival injection may contain about 20 mg, or about 50 mg, or about 75 mg, or about 100 mg, or about 125 mg or about 150 mg, or about 175 mg, or about 200 mg of microspheres, including the incorporated therapeutic component. For non-human individuals, the dimensions and total weight of the microsphere(s) may be larger or smaller, depending on the type of individual.

The dosage of the therapeutic component in the microsphere is generally in the range from about 0.001% to about 100 mg per eye per dose, but also can vary from this depending upon the activity of the agent and its solubility.

Thus, microspheres can be prepared where the center may be of one material and the surface may have one or more layers of the same or a different composition, where the layers may be cross-linked, or of a different molecular weight, different density or porosity, or the like. For example, where it is desirable to quickly release an initial bolus of drug, the center of the microsphere may be a polylactate coated with a polylactate-polyglycolate copolymer, so as to enhance the rate of initial degradation. Alternatively, the center may be polyvinyl alcohol coated with polylactate, so that upon degradation of the polylactate exterior the center would dissolve and be rapidly washed out of the eye.

The microspheres may be of any particulate geometry including micro and nanospheres, micro and nanoparticles, spheres, powders, fragments and the like. The upper limit for the microsphere size will be determined by factors such as toleration for the implant, size limitations on insertion, desired rate of release, ease of handling, etc. Spheres may be in the range of about 0.5 µm to 4 mm in diameter, with comparable volumes for other shaped particles.

The size and form of the microspheres can also be used to control the rate of release, period of treatment, and drug concentration at the site of implantation. Larger microspheres will deliver a proportionately larger dose, but depending on the surface to mass ratio, may have a slower release rate. The particular size and geometry of the microspheres are chosen to suit the activity of the active agent and the location of its target tissue.

The proportions of the cyclic lipid component, polymer, and any other modifiers may be empirically determined by formulating several microsphere batches with varying average proportions. A USP approved method for dissolution or release test can be used to measure the rate of release (USP 23; NF 18 (1995) pp. 1790-1798). For example, using the infinite sink method, a weighed sample of the microspheres is added to a measured volume of a solution containing 0.9% NaCl in water, where the solution volume will be such that the drug concentration is after release is less than 5% of saturation. The mixture is maintained at 37° C. and stirred slowly to maintain the microspheres in suspension. The appearance of the dissolved drug as a function of time may be followed by various methods known in the art, such as spectrophotometrically, HPLC, mass spectroscopy, etc. until the absorbance becomes constant or until greater than 90% of the drug has been released.

In addition to the cyclic lipid component included in the microspheres disclosed herein, the microsphere may also include one or more additional ophthalmically acceptable therapeutic agents. For example, the microspheres may include one or more antihistamines, one or more antibiotics, one or more beta blockers, one or more steroids, one or more antineoplastic agents, one or more immunosuppressive agents, one or more antiviral agents, one or more antioxidant agents, and mixtures thereof. Alternatively, a single injection of microspheres may include two or more microsphere batches each containing a different therapeutic component or components. Such a mixture of different microspheres in included within the present invention so long as a therapeutic component comprises a cyclic lipid.

Additional pharmacologic or therapeutic agents which may find use in the present systems, include, without limitation, those disclosed in U.S. Pat. No. 4,474,451, columns 4-6 and 4,327,725, columns 7-8.

Examples of antihistamines include, and are not limited to, loratadine, hydroxyzine, diphenhydramine, chlorpheniramine, brompheniramine, cyproheptadine, terfenadine, clemastine, triprolidine, carbinoxamine, diphenylpyraline, phenindamine, azatadine, tripelennamine, dexchlorpheniramine, dexbrompheniramine, methdilazine, and trimeprazine doxylamine, pheniramine, pyrilamine, chlorcyclizine, thonzylamine, and derivatives thereof.

Examples of antibiotics include without limitation, cefazolin, cephradine, cefaclor, cephapirin, ceftizoxime, cefoperazone, cefotetan, cefutoxime, cefotaxime, cefadroxil, ceftazidime, cephalexin, cephalothin, cefamandole, cefoxitin, cefonicid, ceforanide, ceftriaxone, cefadroxil, cephradine, cefuroxime, ampicillin, amoxicillin, cyclacillin, ampicillin, penicillin G, penicillin V potassium, piperacillin, oxacillin, bacampicillin, cloxacillin, ticarcillin, azlocillin, carbenicillin, methicillin, nafcillin, erythromycin, tetracycline, doxycycline, minocycline, aztreonam, chloramphenicol, ciprofloxacin hydrochloride, clindamycin, metronidazole, gentamicin, lincomycin, tobramycin, vancomycin, polymyxin B sulfate, colistimethate, colistin, azithromycin, augmentin, sulfamethoxazole, trimethoprim, and derivatives thereof.

Examples of beta blockers include acebutolol, atenolol, labetalol, metoprolol, propranolol, timolol, and derivatives thereof.

Examples of steroids include corticosteroids, such as cortisone, prednisolone, fluorometholone, dexamethasone, medrysone, loteprednol, fluazacort, hydrocortisone, prednisone, betamethasone, prednisone, methylprednisolone, triamcinolone hexacetonide, paramethasone acetate, diflorasone, fluocinonide, fluocinolone, triamcinolone, derivatives thereof, and mixtures thereof.

Examples of antineoplastic agents include adriamycin, cyclophosphamide, actinomycin, bleomycin, daunorubicin, doxorubicin, epirubicin, mitomycin, methotrexate, fluorouracil, carboplatin, carmustine (BCNU), methyl-CCNU, cisplatin, etoposide, interferons, camptothecin and derivatives thereof, phenesterine, taxol and derivatives thereof, taxotere and derivatives thereof, vinblastine, vincristine, tamoxifen, etoposide, piposulfan, cyclophosphamide, and flutamide, and derivatives thereof.

Examples of immunosuppressive agents include cyclosporine, azathioprine, tacrolimus, and derivatives thereof.

Examples of antiviral agents include interferon gamma, zidovudine, amantadine hydrochloride, ribavirin, acyclovir, valacyclovir, dideoxycytidine, phosphonoformic acid, ganciclovir, and derivatives thereof.

Examples of antioxidant agents include ascorbate, alpha-tocopherol, mannitol, reduced glutathione, various carotenoids, cysteine, uric acid, taurine, tyrosine, superoxide dismutase, lutein, zeaxanthin, cryptoxanthin, astaxanthin, lycopene, N-acetyl-cysteine, carnosine, gamma-glutamyl-cysteine, quercetin, lactoferrin, dihydrolipoic acid, citrate, *Ginkgo Biloba* extract, tea catechins, bilberry extract, vitamins E or esters of vitamin E, retinyl palmitate, and derivatives thereof.

Other therapeutic agents include squalamine, carbonic anhydrase inhibitors, alpha-2 adrenergic receptor agonists, antiparasitics, antifungals, and derivatives thereof.

The amount of active agent or agents employed in the microspheres, individually or in combination, will vary widely depending on the effective dosage required and the desired rate of release from the microspheres. Usually the agent will be at least about 1, more usually at least about 10 weight percent of the microsphere, and usually not more than about 80, more usually not more than about 40 weight percent of the microspheres.

Some of the present implants may comprise a cyclic lipid component that comprises a combination of two or more different cyclic lipid derivatives. One microsphere or dosage of microspheres may comprise a combination of bimatoprost and latanoprost. Another microsphere or dosage of microspheres may comprise a combination of bimatoprost and travoprost.

As discussed herein, the present microspheres may comprise additional therapeutic agents. For example, one microsphere or dosage of microspheres may comprise a combination of bimatoprost and a beta-adrenergic receptor antagonist. More specifically, the microsphere or dosage of microspheres may comprise a combination of bimatoprost and Timolol®. Or, a microsphere or dosage of microspheres may comprise a combination of bimatoprost and a carbonic anhydrase inhibitor. For example, the microsphere or dosage of microspheres may comprise a combination of bimatoprost and dorzolamide (Trusopt®).

In addition to the therapeutic component, the microspheres disclosed herein may include or may be provided in compositions that include effective amounts of buffering agents, preservatives and the like. Suitable water soluble buffering agents include, without limitation, alkali and alkaline earth carbonates, phosphates, bicarbonates, citrates, borates, acetates, succinates and the like, such as sodium phosphate, citrate, borate, acetate, bicarbonate, carbonate and the like. These agents advantageously present in amounts sufficient to maintain a pH of the system of between about 2 to about 9 and more preferably about 4 to about 8. As such the buffering agent may be as much as about 5% by weight of the total implant. Suitable water soluble preservatives include sodium bisulfite, sodium bisulfate, sodium thiosulfate, ascorbate, benzalkonium chloride, chlorobutanol, thimerosal, phenylmercuric acetate, phenylmercuric borate, phenylmercuric nitrate, parabens, methylparaben, polyvinyl alcohol, benzyl alcohol, phenylethanol and the like and mixtures thereof. These agents may be present in amounts of from about 0.001% to about 5% by weight and preferably about 0.01% to about 2% by weight. In at least one of the present microspheres, a benzalkonium chloride preservative is provided in the implant, such as when the cyclic lipid component consists essentially of bimatoprost.

In some situations mixtures of microspheres may be utilized employing the same or different pharmacological agents. In this way, a cocktail of release profiles, giving a biphasic or triphasic release with a single administration is achieved, where the pattern of release may be greatly varied.

Additionally, release modulators such as those described in U.S. Pat. No. 5,869,079 may be included in the microspheres. The amount of release modulator employed will be dependent on the desired release profile, the activity of the modulator, and on the release profile of the cyclic lipid component in the absence of modulator. Electrolytes such as sodium chloride and potassium chloride may also be included in the microspheres. Where the buffering agent or enhancer is hydrophilic, it may also act as a release accelerator. Hydrophilic additives act to increase the release rates through faster dissolution of the material surrounding the drug in the microspheres, which increases the surface area of the drug exposed, thereby increasing the rate of drug bioerosion. Similarly, a hydrophobic buffering agent or enhancer dissolves more slowly, slowing the exposure of drug, and thereby slowing the rate of drug bioerosion.

In certain microspheres, the combination of bimatoprost and a biodegradable polymer matrix is released or delivered an amount of bimatoprost between about 0.1 mg to about 0.5 mg for about 3-6 months after implantation into the eye.

Various techniques may be employed to produce the microspheres described herein. Useful techniques include, but are not necessarily limited to, self-emulsification methods, super critical fluid methods, solvent evaporation methods, phase separation methods, spray drying methods, grinding methods, interfacial methods, molding methods, injection molding methods, combinations thereof and the like.

Compression methods may be used to make the implants, and typically yield implants with faster release rates than extrusion methods. Compression methods may use pressures of about 50-150 psi, more preferably about 70-80 psi, even more preferably about 76 psi, and use temperatures of about 0 degrees C. to about 115 degrees C., more preferably about 25 degrees C.

Another method comprises using an oil-in-oil emulsion process to produce the present microparticles.

In one embodiment, a method for producing therapeutic polymeric microparticles comprises encapsulating a cyclic lipid component with a polymeric component to form a population of cyclic lipid-encapsulated microparticles by an oil-in-oil emulsion process. Such microparticles are effective in treating one or more ocular conditions, as described herein, and are suitable for administration to a patient into the subconjunctival space. The therapeutic activity of the cyclic lipid component remains stable during storage of the microspheres which may be attributed to the particular encapsulated form of the microspheres.

In more detail, a method of forming microparticles comprises forming an oil-in-oil emulsion containing the cyclic lipid component and the polymeric component. For example, the method may include mixing or combining a plurality, such as two or more, non-aqueous liquid compositions to form an emulsion. In one embodiment, a first composition may comprise an organic solvent, and a second composition may comprise an oil. At least one of the compositions contains the cyclic lipid component, the polymeric component, or the cyclic lipid component and the polymeric component.

The method also comprises drying the emulsion to form a dried emulsion product. The drying can be achieved using one or more techniques to remove the liquid from the emulsified product. For example, the drying process can include increasing the temperature of or near the emulsified product to facilitate evaporation of the liquid, can include the use of a vacuum to facilitate removal of the liquid, can include centrifugation to separate solid from the liquid, and combinations thereof.

The dried emulsion product can then be contacted with a solvent to form a solvent containing composition. Adding a solvent to the dried emulsion product, or otherwise contacting the product with the solvent results in the product being suspended in a volume of the liquid solvent. The contacting can include a step of stirring or mixing the combination of the solvent and dried emulsion product to form a suspension of the dried emulsion product in the solvent. The suspension can include particles of the dried emulsion product, for example, microspheres of various sizes and shapes, including microparticles.

After forming the solvent containing composition, the method can comprise removing the solvent from the solvent-containing composition to form a population of microparticles that comprise the cyclic lipid component and the polymeric component. The removing can include one or more steps of centrifuging and/or rinsing intermediate compositions, and can include one or more steps of drying the resulting composition. The resulting products are encapsulated microparticles or microimplants that comprise a cyclic lipid component encapsulated by a polymeric component, such as a biodegradable polymer coating.

As discussed herein, the cyclic lipid component can comprises a single type of cyclic lipid derivative or derivatives. In certain embodiments, the cyclic lipid component comprises at least one prostamide derivative selected from the group consisting of bimatoprost, esters thereof, and mixtures thereof. In a further embodiment, the cyclic lipid component consists essentially of bimatoprost.

In additional embodiments, the cyclic lipid component can comprise combinations of two or more different cyclic lipid derivatives, such as a combination of bimatoprost and latanoprost, bimatoprost and travoprost, and the like.

The present methods are effective in producing encapsulated cyclic lipid component microparticles that maintain or preserve a substantial portion, if not all, of the therapeutic activity after a terminal sterilization procedure. It can be understood, that the present methods may also comprise a step of terminally sterilizing the microparticles. The microparticles can be sterilized before packaging or in their packaging. Sterilization of packages containing the present microparticles or implants is often preferred. The method may comprise exposing the present microparticles or implants to sterilizing amounts of gamma radiation, e-beam radiation, and other terminal sterilization products. In one embodiment, a method may comprise a step of exposing the present microparticles to gamma radiation at a dose of about 25 kGy.

As discussed herein, the polymeric component recited in the present method may comprise a biodegradable polymer or biodegradable copolymer. In at least one embodiment, the polymeric component comprises a poly(lactide-co-glycolide) PLGA copolymer. In a further embodiment, the PLGA copolymer has a lactide/glycolide ratio of 75/25. In a still further embodiment, the PLGA copolymer has at least one of a molecular weight of about 63 kilodaltons and an inherent viscosity of about 0.6 dL/g.

The present methods may also comprise a step of forming a first composition which comprises a cyclic lipid component, a polymeric component, and an organic solvent, and a step of forming a second oil-containing composition, and mixing the first composition and the second oil-containing composition.

The present methods may also comprise evaporating the oil-in-oil emulsion to form an evaporated product, as described herein.

Further, the methods may comprise a step of suspending the evaporated product in a solvent before removing the solvent from the solvent containing composition. Such a step can be understood to be a way of forming a suspension.

As one example, a method of forming encapsulated bimatoprost biodegradable microparticles comprises forming an oil-in-oil emulsion comprising the bimatoprost and PLGA, evaporating the liquid from the emulsion to form an evaporated product, suspending and rinsing the evaporated product, and drying the evaporated product.

In accordance with the disclosure herein, an embodiment of the present invention is a population of microparticles that comprise a polymeric component encapsulating a prostamide component in the form of oil-in-oil emulsified microparticles. In one specific embodiment, the polymeric component comprises a PLGA copolymer and the cyclic lipid component comprises at least one prostamide derivative selected from the group consisting of bimatoprost, salts thereof, and mixtures thereof.

The resulting population may be a terminally sterilized population of microparticles. Terminally sterilized microparticles retain their therapeutic activity during storage and therefore can provide successful treatment to patients. In certain embodiments, a major portion of the prostamide component of the terminally sterilized microparticles remains stable. For example, in certain embodiments, at least 80% of the prostamide component remains stable after sterilization. In further embodiments, at least 90%, at least 95%, or at least 99% of the prostamide component remains stable.

In addition, the present population of microparticles may have a maximum particle diameter less than about 200 µm. In certain embodiments, the population of microparticles has an average or mean particle diameter less than about 50 µm. In further embodiments, the population of microparticles has a mean particle diameter from about 30 µm to about 50 µm.

The present microparticles are structured or configured to release the cyclic lipid component for extended periods of time at controlled rates. In some embodiments, the cyclic lipid component is released at a substantially linear rate (e.g., a single rate) over the life of the microparticles (e.g., until the microparticles fully degrade). Other embodiments are capable of releasing the cyclic lipid component at multiple rates or different rates over the life of the microparticles. The rate at which the microparticles degrade can vary, as discussed herein, and therefore, the present microparticles can release the cyclic lipid component for different periods of time depending on the particular configuration and materials of the microparticles. In at least one embodiment, a microparticle can release about 1% of the cyclic lipid component in the microparticles per day. In a further embodiment, the microparticles may have a release rate of about 0.7% per day when measured in vitro. Thus, over a period of about 40 days, about 30% of the cyclic lipid component may have been released.

As discussed herein, the amount of the cyclic lipid component present in the microparticles can vary. In certain embodiments, about 10% wt/wt of the microparticles is the cyclic lipid component. In further embodiments, the cyclic lipid component constitutes about 5% wt/wt of the microparticles.

The microspheres, including the population of microparticles, of the present invention may be inserted into the subconjunctival space of an eye by a variety of methods. The method of placement may influence the therapeutic component or drug release kinetics. A preferred means of administration of the microspheres of the present invention is by subconjunctival injection. The location of the site of injection of the microspheres may influence the concentration gradients of therapeutic component or drug surrounding the element, and thus influence the delivery rate to a given tissue of the eye. For example, an injection into the conjunctiva toward the posterior of the eye will direct drug more efficiently to the tissues of the posterior segment, while a site of injection closer to the anterior of the eye (but avoiding the cornea) may direct drug more efficiently to the anterior segment.

Microparticles may be administered to patients by administering an ophthalmically acceptable composition which comprises the microparticles to the patient. For example, microparticles may be provided in a liquid composition, a suspension, an emulsion, and the like, and administered by injection or implantation into the subconjunctival space of the eye.

The present implants or microparticles are configured to release an amount of cyclic lipid component effective to treat an ocular condition, such as by reducing at least one symptom of the ocular condition. More specifically, the microparticles may be used in a method to treat glaucoma, such as open angle glaucoma, ocular hypertension, chronic angle-closure glaucoma, with patent iridotomy, pseudoexfoliative glaucoma, and pigmentary glaucoma. By injecting the cyclic lipid component-containing microspheres into the subconjunctival space of an eye, it is believed that the cyclic lipid component is effective to enhance aqueous humor flow thereby reducing intraocular pressure. Additionally, the present inventors have shown that subconjunctival delivery of microspheres containing a cyclic lipid component is able to provide quite high concentrations of the therapeutic agent to the retina of the eye.

The microspheres disclosed herein may also be configured to release the cyclic lipid component with or without additional agents, as described above, which to prevent or treat diseases or conditions, such as the following:

MACULOPATHIES/RETINAL DEGENERATION: Non-Exudative Age Related Macular Degeneration (ARMD), Exudative Age Related Macular Degeneration (ARMD), Choroidal Neovascularization, Diabetic Retinopathy, Acute Macular Neuroretinopathy, Central Serous Chorioretinopathy, Cystoid Macular Edema, Diabetic Macular Edema.

UVEITIS/RETINITIS/CHOROIDITIS: Acute Multifocal Placoid Pigment Epitheliopathy, Behcet's Disease, Birdshot Retinochoroidopathy, Infectious (Syphilis, Lyme, Tuberculosis, Toxoplasmosis), Intermediate Uveitis (Pars Planitis), Multifocal Choroiditis, Multiple Evanescent White Dot Syndrome (MEWDS), Ocular Sarcoidosis, Posterior Scleritis, Serpiginous Choroiditis, Subretinal Fibrosis and Uveitis Syndrome, Vogt-Koyanagi-Harada Syndrome.

VASCULAR DISEASES/EXUDATIVE DISEASES: Coat's Disease, Parafoveal Telangiectasis, Papillophlebitis, Frosted Branch, Angiitis, Sickle Cell Retinopathy and other Hemoglobinopathies, Angioid Streaks, Familial Exudative Vitreoretinopathy.

TRAUMATIC/SURGICAL: Sympathetic Ophthalmia, Uveitic Retinal Disease, Retinal Detachment, Trauma, Laser, PDT, Photocoagulation, Hypoperfusion During Surgery, Radiation Retinopathy, Bone Marrow Transplant Retinopathy.

PROLIFERATIVE DISORDERS: Proliferative Vitreal Retinopathy and Epiretinal Membranes, Proliferative Diabetic Retinopathy.

INFECTIOUS DISORDERS: Ocular Histoplasmosis, Ocular Toxocariasis, Presumed Ocular Histoplasmosis Syndrome (POHS), Endophthalmitis, Toxoplasmosis, Retinal Diseases Associated with HIV Infection, Choroidal Disease Associated with HIV Infection, Uveitic Disease Associated with HIV Infection, Viral Retinitis, Acute Retinal Necrosis, Progressive Outer Retinal Necrosis, Fungal Retinal Diseases, Ocular Syphilis, Ocular Tuberculosis, Diffuse Unilateral Subacute Neuroretinitis, Myiasis.

GENETIC DISORDERS: Systemic Disorders with Associated Retinal Dystrophies, Congenital Stationary Night Blindness, Cone Dystrophies, Fundus Flavimaculatus, Best's Disease, Pattern Dystrophy of the Retinal Pigmented Epithelium, X-Linked Retinoschisis, Sorsby's Fundus Dystrophy, Benign Concentric Maculopathy, Bietti's Crystalline Dystrophy, pseudoxanthoma elasticum.

RETINAL TEARS/HOLES: Retinal Detachment, Macular Hole, Giant Retinal Tear.

TUMORS: Retinal Disease Associated with Tumors, Congenital Hypertrophy of the RPE, Posterior Uveal Melanoma, Choroidal Hemangioma, Choroidal Osteoma, Choroidal Metastasis, Combined Hamartoma of the Retina and Retinal Pigmented Epithelium, Retinoblastoma, Vasoproliferative Tumors of the Ocular Fundus, Retinal Astrocytoma, Intraocular Lymphoid Tumors.

MISCELLANEOUS: Punctate Inner Choroidopathy, Acute Posterior Multifocal Placoid Pigment Epitheliopathy, Myopic Retinal Degeneration, Acute Retinal Pigment Epithelitis and the like.

In one embodiment, an implant, such as the microspheres disclosed herein, is administered to a subconjunctival space of an eye.

In at least one embodiment, a method of reducing intraocular pressure in an eye of a patient comprises administering a microsphere containing a cyclic lipid component, as disclosed herein, to a patient by subconjunctival injection. A syringe apparatus including an appropriately sized needle, for example, a 22 gauge needle, a 27 gauge needle or a 30 gauge needle, can be effectively used to inject the composition with into the subconjunctival space of an eye of a human or animal. Frequent repeat injections are often not necessary due to the extended release of the cyclic lipid component from the microspheres.

In addition, for dual therapy approaches to treating an ocular condition, the method may include one or more additional steps of administering additional therapeutic agents to the eye, such as by topically administering compositions containing timolol, dorzolamide, and latoprost, among others.

In another aspect of the invention, kits and packages for treating an ocular condition of the eye are provided, comprising: a) a container comprising an extended release microsphere formulation comprising a therapeutic component including a cyclic lipid component, such as bimatoprost (Lumigan®), and a drug release sustaining component; and b) instructions for use. Instructions may include steps of how to handle the microspheres, how to insert the microspheres into an ocular region, and what to expect from using the microspheres.

In certain implants, the microspheres preparation comprises a therapeutic component which consists essentially of bimatoprost, salts thereof, and mixtures thereof, and a biodegradable polymer matrix. The biodegradable polymer matrix may consist essentially of PLA, PLGA, or a combination thereof. When placed in the eye, the preparation releases about 40% to about 60% of the bimatoprost to provide a loading dose of the bimatoprost within about one day after subconjunctival administration. Subsequently, the microspheres release about 1% to about 2% of the bimatoprost per day to provide a sustained therapeutic effect. Such microsphere preparations may be effective in reducing and maintaining a reduced intraocular pressure, such as below about 15 mm Hg for several months, and potentially for one or two years.

Other microspheres disclosed herein may be configured such that the amount of the cyclic lipid component that is released from the microspheres within two days of subconjunctival injection is less than about 95% of the total amount of the cyclic lipid component in the microsphere. In certain formulations, 95% of the cyclic lipid component is not released until after about one week of injection. In certain microsphere formulations, about 50% of the cyclic lipid component is released within about one day of placement in the eye, and about 2% is released for about 1 month after being placed in the eye. In other microspheres, about 50% of the cyclic lipid component is released within about one day of subconjunctival administration, and about 1% is released for about 2 months after such administration.

In an alternative embodiment, the present invention may comprise the installation of a hollow depot device, made from a biocompatible, preferably non-biodegradable, polymer in connection with and preferably penetrating the conjunctiva of an eye. Such a device is described, for example, in US Patent Publication 20050112175, hereby incorporated by reference herein. The depot is preferably refillable with microspheres comprising an ophthalmically active therapeutic component, such as an ophthalmically active cyclic lipid component.

EXAMPLES

Example 1

Manufacture and Testing of Implants Containing Bimatoprost and a Biodegradable Polymer Matrix Biodegradable implants were made by combining bimatoprost with a biodegradable polymer composition. 800 mg of polylactic acid (PLA) was combined with 200 mg of bimatoprost. The combination was dissolved in 25 milliliters of dichloromethane. The mixture was placed in a vacuum at 45° C. overnight to evaporate the dichloromethane. The resulting mixture was in the form of a cast sheet. The cast sheet was cut and ground in a high shear grinder with dry ice until the particles could pass through a sieve having a pore size of about 125 μm. The percent of bimatoprost present in the microparticles was analyzed using high pressure liquid chromatography (HPLC). The percent release of bimatoprost from the microparticles was profiled using dialysis. The percent of bimatoprost remaining in the recovered particles was analyzed by HPLC.

The release profile is described in Table 1.

| Time Point | Elapsed Time (Days) | Percent Released | Percent Per Day |
|---|---|---|---|
| Start | 0 | — | — |
| 1 | 1.03 | 47.51 | 47.51 |
| 2 | 2.03 | 47.92 | 0.41 |
| 3 | 3.03 | 49.99 | 2.07 |
| 4 | 4.03 | 50.09 | 0.10 |
| 5 | 7.04 | 50.90 | 0.82 |

The percent loading of bimatoprost was 14.93%. The percent of bimatoprost remaining in the recovered release particles was 4.94%.

Example 2

Extrusion Process and Compression of Manufacturing Bimatoprost-containing Biodegradable Intraocular Implants Bimatoprost is combined with a biodegradable polymer composition in a mortar. The combination is mixed with a shaker set at about 96 RPM for about 15 minutes. The powder blend is scraped off the wall of the mortar and is then remixed for an additional 15 minutes. The mixed powder blend is heated to a semi-molten state at specified temperature for a total of 30 minutes, forming a polymer/drug melt.

Rods are manufactured by pelletizing the polymer/drug melt using a 9 gauge polytetrafluoroethylene (PTFE) tubing, loading the pellet into the barrel and extruding the material at the specified core extrusion temperature into filaments. The filaments are then cut into about 1 mg size implants or drug delivery systems. The rods may have dimensions of about 2 mm long×0.72 mm diameter. The rod implants weigh between about 900 μg and 1100 μg.

Wafers are formed by flattening the polymer melt with a Carver press at a specified temperature and cutting the flattened material into wafers, each weighing about 1 mg. The wafers have a diameter of about 2.5 mm and a thickness of about 0.13 mm. The wafer implants weigh between about 900 μg and 1100 μg.

In-vitro release testing is performed by placing each implant into a 24 mL screw cap vial with 10 mL of Phosphate Buffered Saline solution at 37° C. 1 mL aliquots are removed and are replaced with equal volume of fresh medium on day 1, 4, 7, 14, 28, and every two weeks thereafter.

Drug assays are performed by HPLC, which consists of a Waters 2690 Separation Module (or 2696), and a Waters 2996 Photodiode Array Detector. An Ultrasphere, C-18(2), 5 μm; 4.6×150 mm column heated at 30° C. is used for separation and the detector is set at about 264 nm. The mobile phase is (10:90) MeOH-buffered mobile phase with a flow rate of 1 mL/min and a total run time of 12 min per sample. The buffered mobile phase may comprise (68:0.75: 0.25:31) 13 mM 1-Heptane Sulfonic Acid, sodium salt-glacial acetic acid-triethylamine-Methanol. The release rates are determined by calculating the amount of drug being released in a given volume of medium over time in μg/day.

Polymers which may be used in the implants can be obtained from Boehringer Ingelheim. Examples of polymer include: RG502, RG752, R202H, R203 and R206, and Purac PDLG (50/50). RG502 is (50:50) poly(D,L-lactide-co-glycolide), RG752 is (75:25) poly(D,L-lactide-co-glycolide), R202H is 100% poly(D, L-lactide) with acid end group or terminal acid groups, R203 and R206 are both 100% poly(D, L-lactide). Purac PDLG (50/50) is (50:50) poly(D,L-lactide-co-glycolide). The inherent viscosity of RG502, RG752, R202H, R203, R206, and Purac PDLG are 0.2, 0.2, 0.2, 0.3, 1.0, and 0.2 dL/g, respectively. The average molecular weight of RG502, RG752, R202H, R203, R206, and Purac PDLG are, 11700, 11200, 6500, 14000, 63300, and 9700 daltons, respectively.

Example 3

Bimatoprost/PLA/PLGA Intraocular Implants to Treat Glaucoma

A 72 year old female suffering from glaucoma in both eyes receives an intraocular implant containing bimatoprost and a combination of a PLA and PLGA in each eye. The implants weigh about 1 mg, and contain about 500 mg of bimatoprost. One implant is placed in the vitreous of each eye using a syringe. In about two days, the patient reports a substantial relief in ocular comfort. Examination reveals that the intraocular pressure has decreased, the average intraocular pressure measured at 8:00 AM has decreased from 28 mm Hg to 14.3 mm Hg. The patient is monitored monthly for about 6 months. Intraocular pressure levels remain below 15 mm Hg for six months, and the patient reports reduced ocular discomfort.

Example 4

Bimatoprost/PLA Intraocular Implants to Reduce Ocular Hypertension

A 62 year old male presents with an intraocular pressure in his left eye of 33 mm Hg. An implant containing 400 mg of bimatoprost and 600 mg of PLA is inserted into the vitreous of the left eye using a trocar. The patient's intraocular pressure is monitored daily for one week, and then monthly thereafter. One day after implantation, the intraocular pressure is reduced to 18 mm Hg. By day 7 after implantation, the intraocular pressure is relatively stable at 14 mm Hg. The patient does not experience any further signs of elevated intraocular pressure for 2 years.

Example 5

Oil in Oil Method for Microencapsulation of a Prostamide Derivative

This example describes a process for producing microparticles that include a prostamide derivative encapsulated by a biodegradable polymer. In the specific example, bimatoprost was used as the prostamide derivative. The procedures outlined herein can be used to make encapsulated microparticles of other prostamide derivatives as well.

FIG. 1 is a flow chart illustrating the steps used in the method of this example.

As shown in FIG. 1, a first composition was formed by adding 100 mg of bimatoprost to 20 mL of acetonitrile (CH₃CN) in an Erlenmeyer flask with a magnetic stirrer and stopper. The bimatoprost was solubilized in the acetonitrile. PLGA (900 mg) was added to the solubilized composition and stirred until the PLGA was solubilized. This first composition can be understood to be a discontinuous phase or an acetonitrile phase composition.

A second composition was formed by combining 800 mL of cottonseed oil and 12.8 mL of Span® 85 in a 1000 mL beaker. Span® 85 is a fatty acid composition which comprises oleic acid (C18:1) approx. 74%; linoleic acid (C18:2) approx. 7%; linolenic acid (C18:2) approx. 2%; palmitoleic acid (C16:1) approx. 7%; and palmitic acid (C16:0). Span is a registered trademark of ICI Americas, Inc., and the Span® 85 can be obtained from public sources, such as Sigma Aldrich. Other Span® products can also be used, such as Span® 80. This composition can be understood to be a continuous phase or oil-containing composition.

An emulsion was formed by adding the first composition to the second composition. The speed impeller was set at 350 rotations per minute (rpm) to stir the second composition. The first composition was added to the stirring second composition, and the mixture was allowed to stir for 90 minutes.

The emulsion was then evaporated under filter air flow for 45 hours at 250 rpm air flow.

Hexane (250 mL) was added to the evaporated product and stirred for 1 hour. Subsequently, the suspension was centrifuged at 7000 rpm for 10 minutes.

The pellet containing microparticles was rinsed twice by centrifuging with 100 mL of hexane. The microparticles were resuspended in 15 mL of hexane.

The microspheres were then dried under filter air flow overnight.

Microspheres were packaged under nitrogen and reduced temperatures to maintain the temperature at about 5 C. The cooled microspheres were sterilized using gamma radiation (25-35 kGy).

Figure 2A:
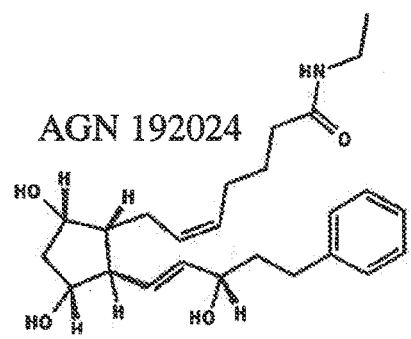
FIG. 2A is the chemical structure of bimatoprost.
Figure 2B:
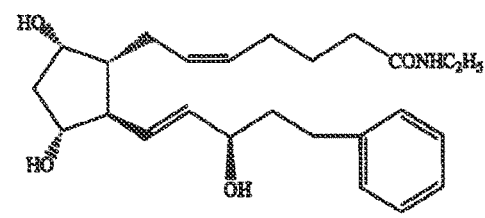
FIG. 2B is the chemical structure of 15β bimatoprost.
Figure 2C:
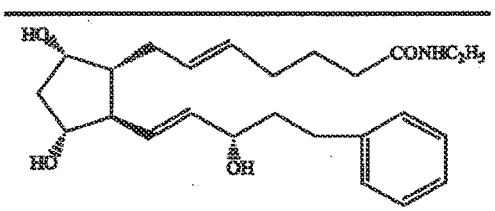
FIG. 2C is the chemical structure of trans 5,6-trans bimatoprost isomer.
Figure 2D:
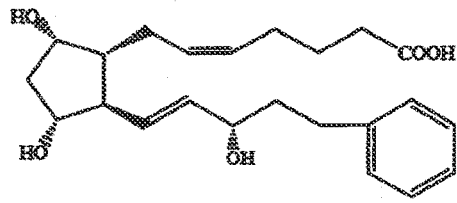
FIG. 2D is the chemical structure of the C1 acid of bimatoprost.
Figure 2E:
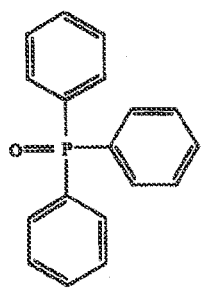
FIG. 2E is the chemical structure of triphenylphosphine oxide.
Figure 2F:
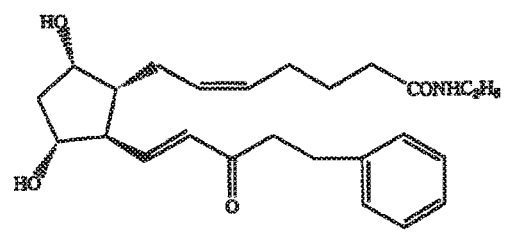
FIG. 2F is the chemical structure of 15-Keto bimatoprost.

FIGS. 2A, 2B, 2C, 2D, 2E, and 2F illustrate the chemical structure of bimatoprost (AGN 192024, FIG. 2A), 1513 bimatoprost (FIG. 2B); 5,6-trans bimatoprost isomer (FIG. 2C); C1 acid of bimatoprost (FIG. 2D); triphenylphosphine oxide (TPPO; FIG. 2E); and 15-Keto bimatoprost (FIG. 2F). Bimatoprost is the active ingredient and the other chemicals are impurities that may be present. Bimatoprost has a molecular weight of 415.6 g/mol, a solubility in water at room temperature of 3.2 mg/mL (which is slightly soluble), and a partition coefficient Log P of 2.4 plus or minus 0.1. Bimatoprost is a non-ionizable compound.

The effects of gamma sterilization on the stability of bimatoprost are presented in the following table (Table 2). The formula abbreviations correspond to compounds illustrated in FIGS. 2A-2F.

|  | Bimatoprost | | | |
|---|---|---|---|---|
|  | % wt/wt bimatoprost | % wt/wt, 15-keto | % wt/wt 15β | % wt/wt 5,6-trans |
| none sterilized | 95.3 | 1.0 | 0.2 | 0.1 |
| gamma sterilized | 85.3 | 2.3 | 0.1 | 0.1 |

Gamma sterilization appeared to decrease the amount of active bimatoprost by about 10%. Gamma sterilization may also change the color of the material (e.g., from white to a yellow/brown) and the consistency of the material (e.g., from a fluffy powder to a more compact powder).

Two separate batches of microparticles were produced using PLGA copolymers from different suppliers, as presented in Table 3, below

| Supplier | Batch Number | Lactide/Glycolide ratio Random/Block End-groups | Molecular Weight | Inherent Viscosity |
|---|---|---|---|---|
| APT | 1 | 75/25 Random Ester & Hydroxyl | 63,200 Da | 0.65 dL/g |
| BPI | 2 | 75/25 Random Ester & Hydroxyl | ~97,100 Da | 0.67 dL/g |

APT in Table 3 refers to Absorbable Polymer Technologies, and BPI refers to Birmingham Polymers, Inc. The PLGA obtained from APT appeared to provide better results than PLGA from BPI.

Figure 3A:
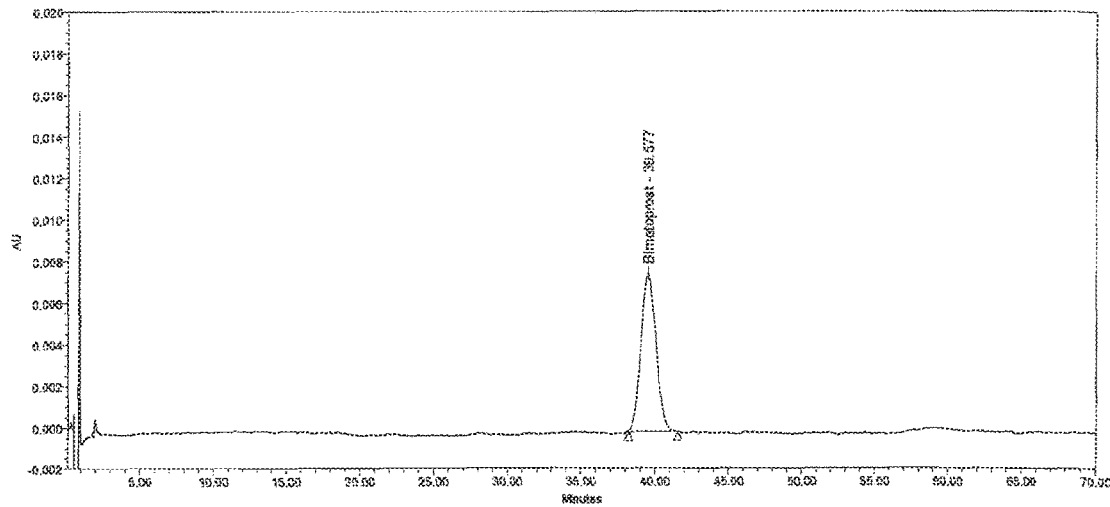
FIG. 3A is a chromatogram of a bimatoprost standard.
Figure 3B:
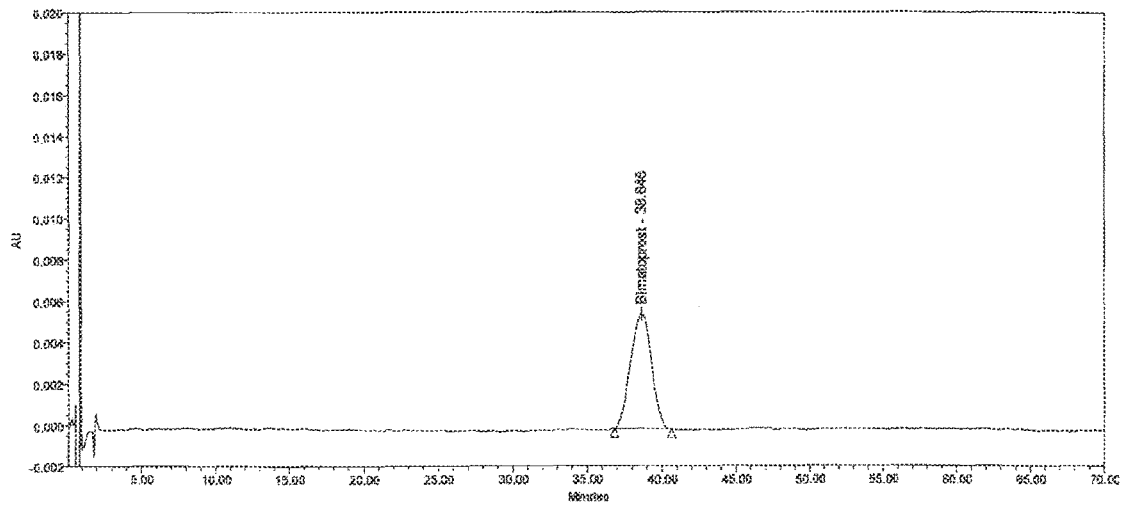
FIG. 3B is a chromatogram of non-sterilized bimatoprost microparticles.
Figure 3C:
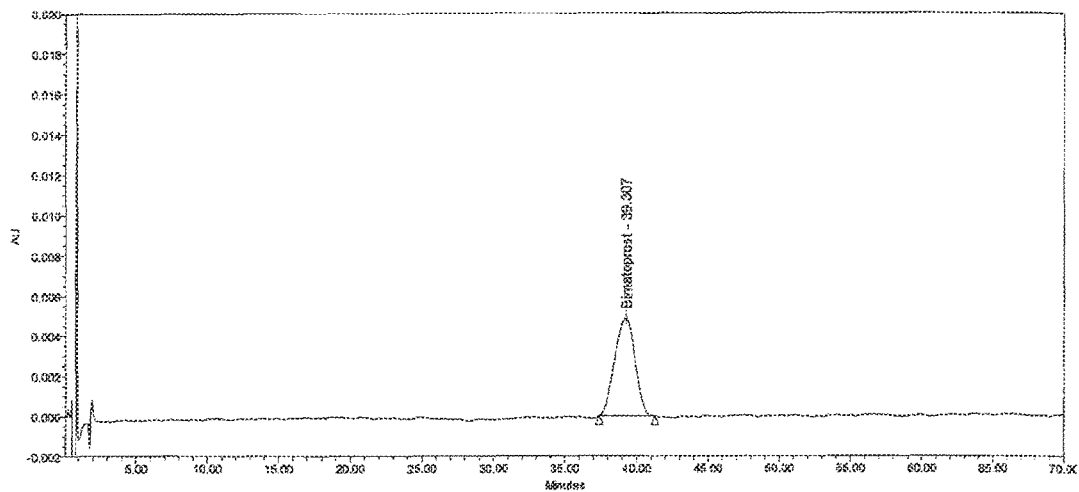
FIG. 3C is a chromatogram of sterilized bimatoprost microparticles.
Figure 3D:
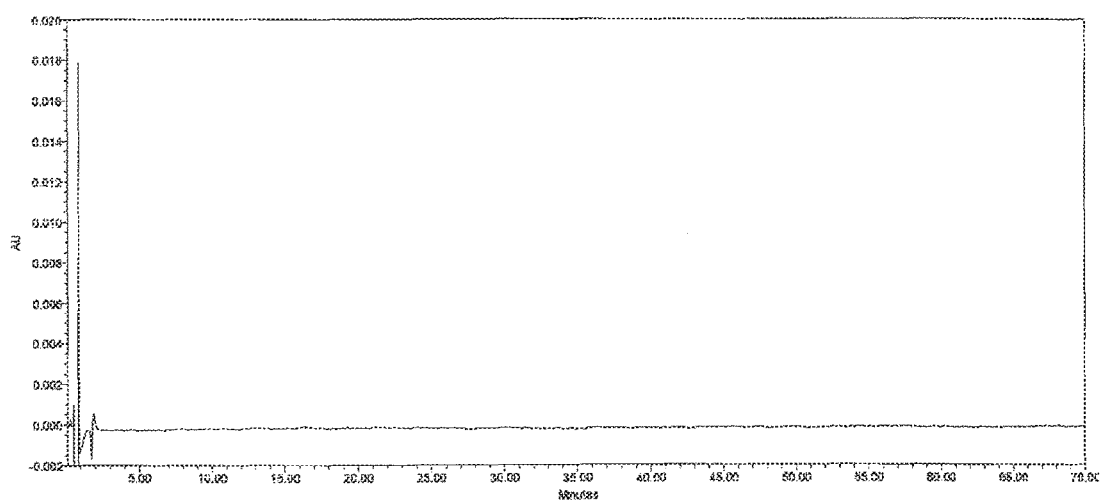
FIG. 3D is a chromatogram of non-sterilized placebo compositions.
Figure 3E:
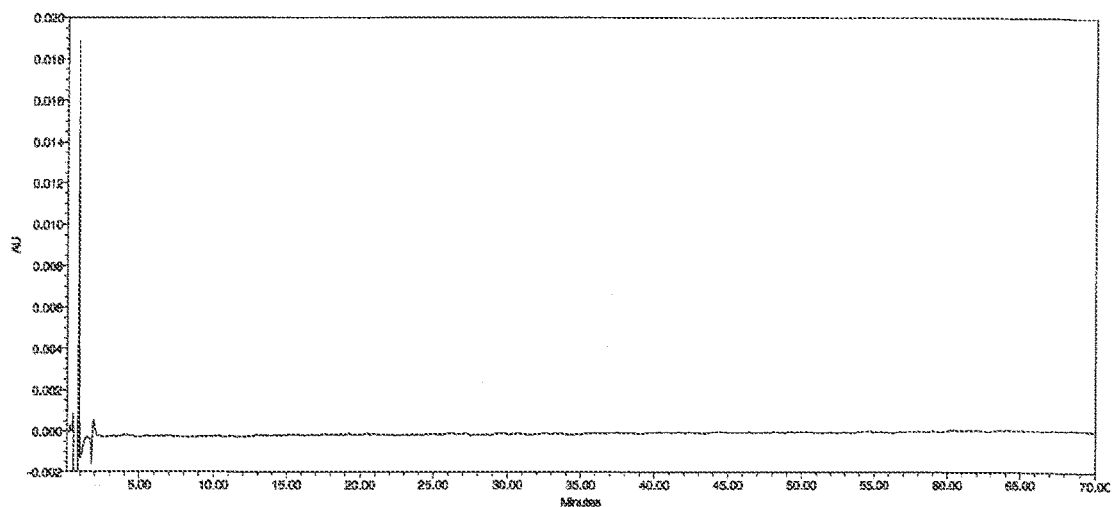
FIG. 3E is a chromatogram of sterilized placebo compositions.

High performance liquid chromatography was used to quantify bimatoprost and impurities present in the microparticles. Analytes were eluted from a Waters Symmetry® C18 reverse-phase column using a mobile phase composed of 72/18/10 (water/acetonitrile/methanol v/v/v) containing 0.03% (w/v) trifluoroacetic acid. UV detection was performed at 210 nm. Chromatograms of a bimatoprost standard (FIG. 3A), a non-sterilized and sterilized placebo compositions (FIG. 3D and FIG. 3E), and non-sterilized and sterilized bimatoprost microparticles (FIG. 3B and FIG. 3C) revealed that the microparticles did not contain detectable amounts of impurities as evidenced by the single absorption peak in FIGS. 3A-C.

Figure 4A:
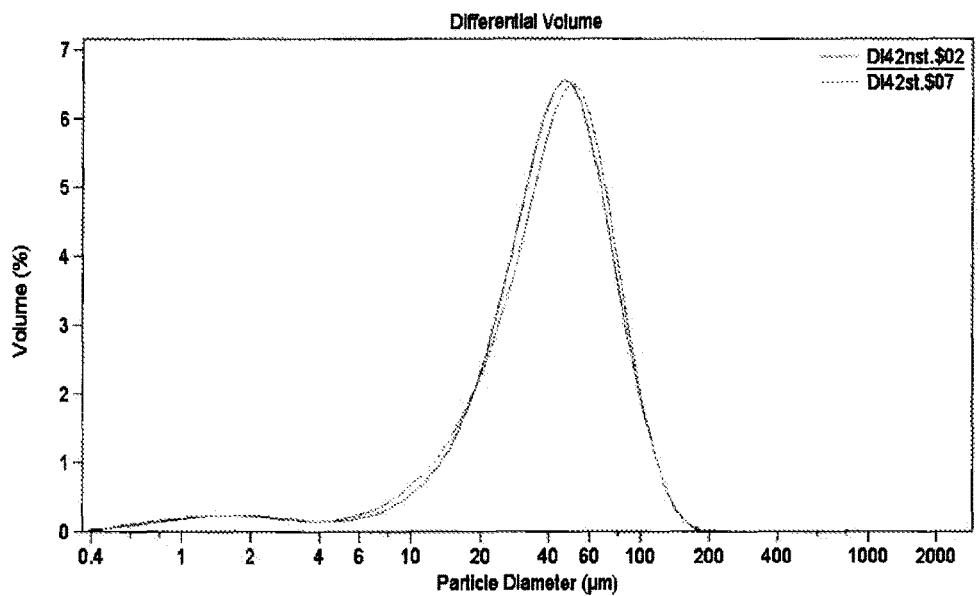
FIG. 4A is a graph of volume % as a function of particle diameter.
Figure 4B:
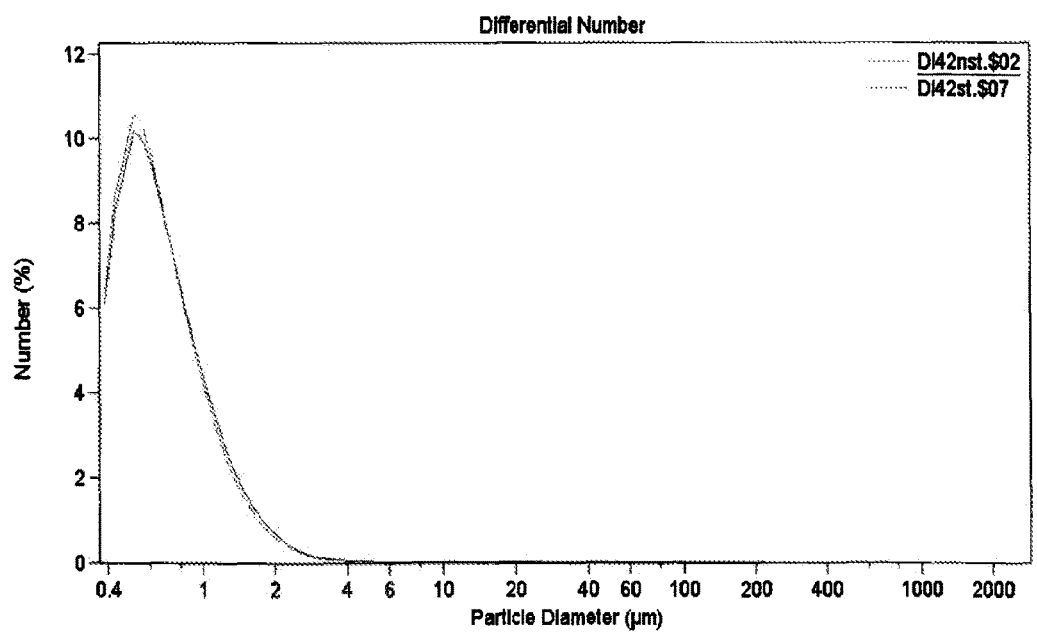
FIG. 4B is a graph of number % as a function of particle diameter.
Figure 4C:
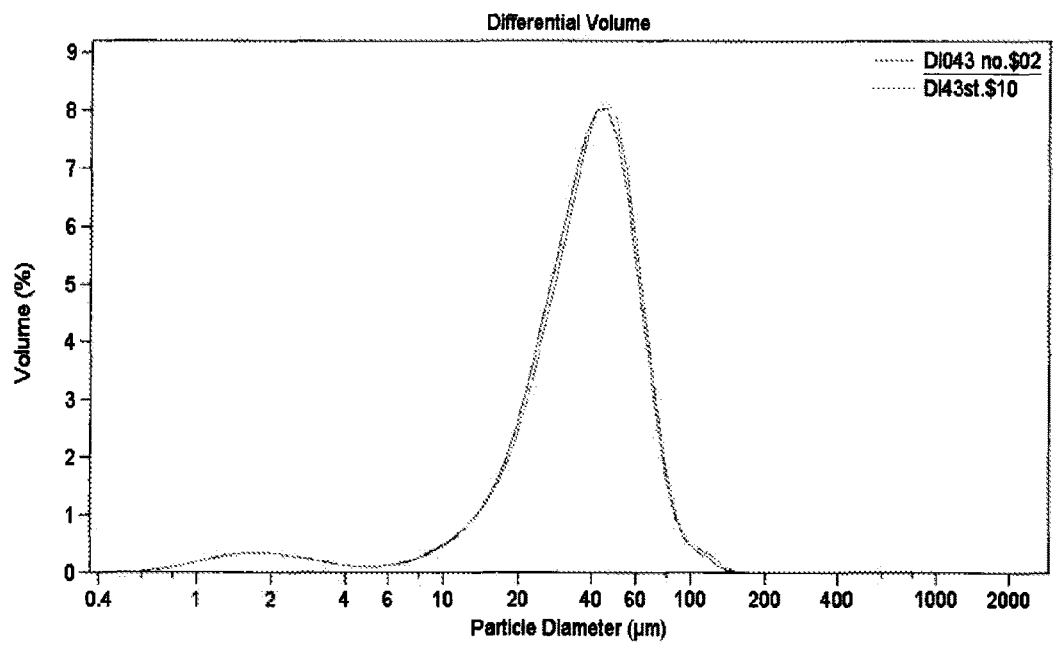
FIG. 4C is a graph of volume % as a function of particle diameter for a different batch of microparticles than shown in FIG. 4A.
Figure 4D:
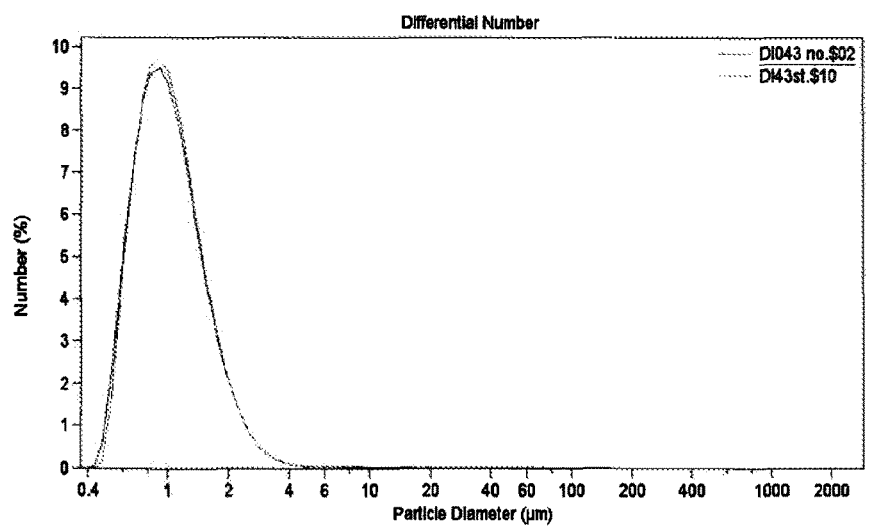
FIG. 4D is a graph of number % as a function of particle diameter for the batch of FIG. 4C.

Particle size was determined by suspending an aliquot of the bimatoprost microspheres in 1 mL of deionized water. To this, 100 μL of 10% Tween 80 was added. The composition was sonicated for 5 minutes and vortexed for 15 seconds. A Coulter LS230 apparatus or equivalent apparatus were used to measure particle size. Mean particle diameters of tested batches were between about 30 μm and about 50 μm. Some particles had diameters up to about 200 μm. These larger particles were observed in batches that were not sieved. FIGS. 4A-4D illustrate particle diameters (differential volume and number) profile superposition for sterile and non sterile conditions. Each graph illustrates the particle diameter distribution for a batch of sterile microspheres and non-sterile microspheres. The data reveal that sterilization did not significantly impact the particle size distribution as evidenced by the substantial overlap in the distribution curves. FIG. 4A illustrates volume % as a function of particle diameter for batch DL042 (top left panel), FIG. 4B illustrates number % as a function of particle diameter for batch DL042 (top right panel), FIG. 4C illustrates volume % as a function of particle diameter for batch DL043 (bottom left panel), and FIG. 4D illustrates number % as a function of particle diameter for batch DL043 (bottom right panel).

Microscopic aspect was determined using the sample prepared for particle size determination, described above. Observations were performed at magnification 5 and 20. FIGS. 5A-5F illustrate shapes of four different non-sterile and two different sterile batches of microspheres (FIG. 5A and FIG. 5B (top two panels) and FIGS. 5C and 5E illustrate non-sterile batches and FIG. 5D and FIG. 5F (bottom two right panels) illustrate sterile batches of microspheres).

Figure 6:
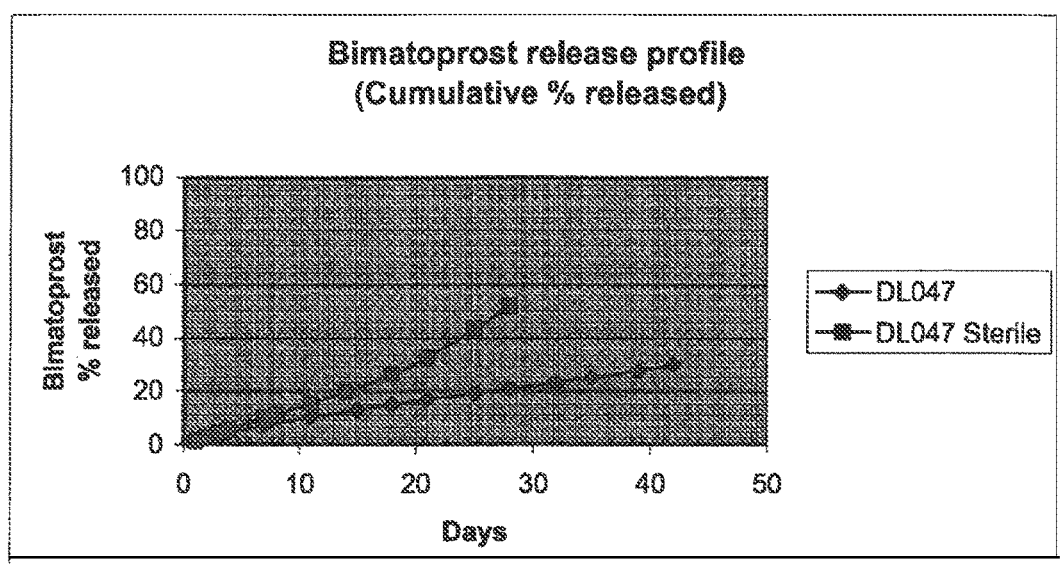
FIG. 6 is a graph percent bimatoprost released as a function of time.

The dissolution profile for a batch of microparticles was monitored for 28 and 42 days for sterile and non-sterile microspheres using dialysis bags and dissolution media. The dissolution media was phosphate buffer (pH 7.4) and ethanol in a ratio of 90/10. Samples were monitored at 37 C in a shaker water bath at approximately 110 rpm. At each time point, an aliquot of sample was collected and replaced by fresh media. The dissolution profile for a batch of sterile and non-sterile microspheres is shown in FIG. 6. The dissolution rate for the non-sterile microparticles was about 0.7%/day (e.g., 30% released over 42 days). The dissolution rate for the sterile batch initially appeared to be about 0.7%/day and increased after about two weeks. FIG. 6 also shows that bimatoprost was released faster from gamma sterilized microspheres than non-sterilized microspheres.

Table 4 below provides information regarding the batches of microspheres prepared in accordance with the present methods and as discussed above.

| Batch No. | PLGA type/SPAN type | Sterilized (Yes/No) |
| --- | --- | --- |
| DL040 | PLGA APT 75/25/ iv 0.65/SPAN 80 | No |
| DL041 | APT/SPAN 85 | No |
| DL042 | APT/SPAN 80 | No |
| DL042 | APT/SPAN 80 | Yes |
| DL043 | APT/SPAN 80 | No |
| DL043 | APT/SPAN 80 | Yes |

In Table 4, APT refers to the PLGA supplier, as discussed herein, iv refers to inherent viscosity, and SPAN refers to the fatty acid composition described herein, and which is publicly available.

Table 5 below provides information regarding the amount of bimatoprost present in non-sterile microspheres. In these microspheres, bimatoprost was present in an amount of about 5% w/w.

| Batch No. | Targeted loading | % w/w bimatoprost |
| --- | --- | --- |
| DL040 | 10% | 4.6 |
| DL041 | 10% | 5.1 |
| DL042 | 10% | 4.8 |
| DL043 | Placebo | ND |

Batches DL042 and DL043 were gamma sterilized (25-35 kGy) in order to evaluate the stability of the active ingredient when encapsulated within PLGA. The results are presented in Table 6 below.

| Batch No. | Targeted Loading | % w/w bimatoprost | % w/w keto |
| --- | --- | --- | --- |
| DL042 | 10% | 4.3 | ND |
| DL042 sterile | 10% | 4.2 | ND |
| DL043 | Placebo | ND | ND |
| DL043 sterile | Placebo | ND | ND |

Example 6

Preparation of Bimatoprost Microspheres

A series of three (3) bimatoprost microsphere (microparticle) formulations, designated Formulations 1, 2 and 3, were prepared as follows:

Formulations 1 and 2 were prepared using a spray-drying technique. Bimatoprost was dissolved in a solution of a polylactide(co-glycolide) (PLGA) biodegradable polymer and dichloromethane at a theoretical bimatoprost content of 3 wt %. Different PLGA polymers were used in each of Formulations 1 and 2. The solution was atomized using a Buchi Model 190 spray dryer with an inlet temperature set at 40° C. The bimatoprost/PLGA polymer microparticles thus formed were recovered for testing.

Formulation 3 was prepared using a solvent-extraction "continuous" microencapsulation process. The bimatoprost was suspended in a solution of a PLGA polymer and ethyl acetate at a theoretical bimatoprost content of 4.3 wt %. The solution was homogenized in the presence of a polyvinyl alcohol solution saturated with 4 mg/mL bimatoprost to produce a water-in-oil emulsion. The microparticles were formed upon extraction of the solvent in a continuous flow of purified water. The microparticles were isolated by centrifugation and lyophilized. The dried particles were then suspended and stirred in purified water at room temperature for approximately 2 hours. The particles were again isolated by centrifugation and lyophilized.

All of the microparticles of Formulations 1, 2 and 3 microparticles were irradiated with 2.5 Mrad gamma radiation prior to use in the rabbit in vivo study, described in Example 8, supra.

Analytical characterization of the microparticles was performed, and the analytical data are summarized in Table 7.

TABLE 7

Summary of characterization data of Bimatoprost Microparticle Formulations.

| Formulation Number | Bimatoprost Content, wt % | Encapsulation Efficiency | Particle Size Distribution, microns | | | Residual Solvent, wt % |
| --- | --- | --- | --- | --- | --- | --- |
| | | | d10 | d90 | Mean | |
| 1 | 2.9 | 96.7 | 1.8 | 30.3 | 14.4 | <0.1 |
| 2 | 2.9 | 96.7 | 1.4 | 17.6 | 8.8 | <0.1 |
| 3 | 4.0 | 88.9 | 2.4 | 41.4 | 19.0 | 0.8 |

Example 7

In Vitro Testing of Bimatoprost Microspheres

Samples of each of the Example 6 Formulations 1, 2 and 3, both irradiated with gamma radiation (as set forth in Example 6) and non-irradiated, were tested in vitro for rate of release of bimatoprost. These in vitro tests were conducted as follows:

Each individual sample of microparticles was placed in a glass vial filled with receptor medium (9% NaCl in water). To allow for "infinite sink" conditions, the receptor medium volume was chosen so that the concentration of bimatoprost would never exceed 5% of saturation. To minimize secondary transport phenomena, e.g. concentration polarization in the stagnant boundary layer, each of the glass vials was placed into a shaking water bath at 37° C. Samples were taken for HPLC analysis from each vial at defined time points. The HPLC method was as described in USP 23 (1995) pp. 1791-1798. The concentration values were used to calculate the cumulative release profiles.

Figure 7:
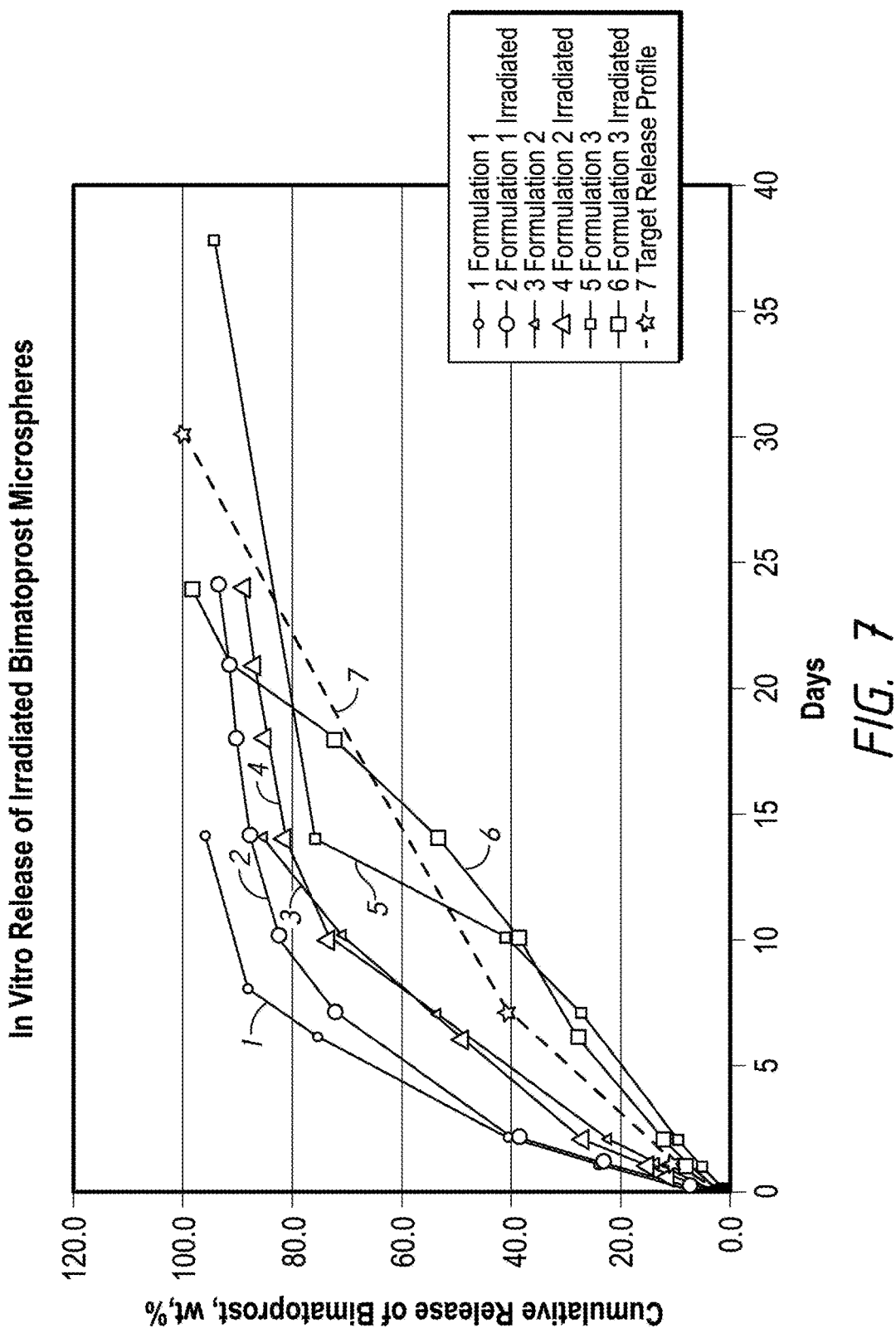
FIG. 7 is a plot of the in vitro release of drug from irradiated and non-irradiated microspheres.

The release profiles are shown in FIG. 7.

As shown in FIG. 7, for each of the samples of Formulations 1 and 2, both irradiated and not irradiated, the release rate of bimatoprost is somewhat faster than the target release rate 7. The samples of Formulation 3, both irradiated and not irradiated, reasonably approximate the target release rate 7.

These data demonstrate that bimatoprost/polymer microparticles can be produced with different release rates, for example, for use in different applications and/or to treat different conditions/diseases. In short, these data demonstrate that bimatoprost/polymer microparticles can be produced with a range of bimatoprost release profiles as needed to treat different ocular conditions and/or to improve visual acuity.

Example 8

Subconjunctivally Injected Bimatoprost Microspheres

A study of subconjunctival injection in New Zealand white rabbit eyes of the Formulation 1, 2 and 3 microparticles of Example 6 was carried out.

The Formulation 1, 2 and 3 microparticles were provided in the form of dry particulates as six-seven doses per vial. A duplicate set of vials was supplied for each formulation, dose level, and timepoint (i.e., 20 vials for each lot number).

A 2 mg/mL bimatoprost solution (Formulation 4) prepared in saline containing 0.1 wt % Tween 80 was provided for dose administration to any animals still available following completion of microparticle dosing.

Preparation: The microparticles in each vial were reconstituted in 2.2 mL of injection vehicle. Microparticle/vehicle compositions were used immediately upon reconstitution or as soon as possible within 2 hours of reconstitution. Details of test composition preparation are outlined in Table 8 below.

TABLE 8

| Formulation Number | Bimatoprost content (wt %) | No. of vials of 6-7 doses | Microspheres per vial (mg) | Vol. of injection vehicle added (mL) | Suspension Conc. (wt %) | Dose volume (mL) |
|---|---|---|---|---|---|---|
| 1 | 2.9 | 10 | 168 | 2.2 | 7.1 | 0.15 |
|  |  | 10 | 336 | 2.2 | 13.2 | 0.15 |
| 2 | 2.9 | 10 | 168 | 2.2 | 7.1 | 0.15 |
|  |  | 10 | 336 | 2.2 | 13.2 | 0.15 |
| 3 | 3.9 | 10 | 139 | 2.2 | 6.2 | 0.15 |
|  |  | 10 | 278 | 2.2 | 11.2 | 0.15 |
| 4 | 2 mg/mL | 10 mL | none | 10 mL | 2 mg/mL | 0.15 |

The injection vehicle was a sterile, aqueous saline solution containing 0.1 wt % Tween 80 (polyoxyethylenesorbitan monooleate).

To ensure that the appropriate dose of microparticles was injected, the following procedure was used to administer the microparticle doses.

An 18-gauge needle was inserted into a vial of sterile injection vehicle to release the vacuum. An empty syringe was attached to the needle the vial containing the vehicle was inverted, and the appropriate volume (2.2 mL) of vehicle was drawn out. The needle and the syringe was withdrawn from the vial containing the vehicle, and the needle was inserted into the vial containing the microparticles to be injected. The vial of microparticles was vented by inserting a separate needle through the septum. Then, leaving this needle in place, the vehicle was injected into the vial containing the microparticles, and both needles were withdrawn.

To suspend the microparticles in the vehicle, the vial was vigorously shaken for at least 30 seconds. After the microparticles were well dispersed, the appropriate amount of suspension (0.20 mL) was pulled into a 1-cc syringe using an 18-gauge needle. The needle was cleared of any suspension by pulling all of the contents into the syringe.

The 18-gauge needle was replaced with a 25-gauge×⅝-inch needle, and the needle was purged of air. The microparticles were injected quickly to prevent the microparticles from settling out of solution. Between each injection, the microparticles were resuspended by agitating the sample vial.

The entire procedure was repeated as necessary to complete dose administration. Each vial was used for a maximum of six to seven injections.

The microparticle doses were stored at −20° C. and then allowed to equilibrate to room temperature for approximately 1-2 hours prior to reconstitution. The injection vehicle was stored at room temperature.

The animals were provided with approximately 150 grams of Teklad Certified High-Fiber Rabbit Diet daily. The animals were provided tap water ad libitum.

Prior to placement on study, a physical examination was performed on each animal. Each animal also had a pre-treatment ophthalmic examination (slit lamp and indirect ophthalmoscopy), performed by a veterinary ophthalmologist.

Prior to placement on study, intraocular pressure (IOP) was determined for both eyes of each animal. Proparacaine hydrochloride 0.5% (1-2 drops) was delivered to each eye prior to measurements.

Neomycin/Polymyxin/Bacitracin (NPB) Ophthalmic Ointment was placed in both eyes of each animal once daily on the day prior to injection (Day −1) and two days after injection (Days 2 and 3).

Prior to dosing, the animals were weighed and randomly assigned to 33 study groups (Groups A-GG). If any alternate animals remained following completion of microsphere dosing for Groups A-GG, these animals were assigned to Groups HH, II, and/or JJ.

Animals were anesthetized with an intravenous injection of a ketamine/xylazine cocktail (87 mg/mL ketamine, 13 mg/mL xylazine) at a volume of 0.1-0.2 mL/kg. Animals instead were anesthetized with an intramuscular injection of ketamine 100 mg/mL at 35 mg/kg plus xylazine 100 mg/mL at 7 mg/kg.

Eyes were prepared for injection as follows: Approximately five minutes prior to injection, eyes were moistened with an ophthalmic Betadine solution. After five minutes, the Betadine was washed out of the eyes with sterile saline. Proparacaine hydrochloride 0.5% (1-2 drops) was delivered to each eye.

On Day 1, each rabbit in Groups A-GG received a 150-W, subconjunctival injection of the appropriate microparticle formulation into the left eye using a 25-gauge×⅝-inch needle. Each rabbit assigned to Groups HH-JJ received a 150-μL, subconjunctival injection of bimatoprost solution into the left eye using a 30-gauge×⅝-inch needle. The bulbar conjunctiva in the dorsal temporal quadrant was elevated using forceps. Microparticle formulation or bimatoprost solution was injected into the subconjunctival space. The actual dose delivered was calculated as a differential of the syringe weight before and after dosing. Injection was performed by board-certified veterinary ophthalmic surgeons.

The animals were observed for mortality/morbidity twice daily.

If an animal was determined to be moribund or under severe distress, the animal was euthanized with an intravenous injection of commercial euthanasia solution. Both eyes were explanted, placed in 10% formalin, and stored for possible future evaluation.

The animals were weighed at random, on Day 1, and prior to necropsy.

Intraocular pressure (IOP) was determined for both eyes of each remaining animal on Days 2, 8±1, 15±1, 22±1, and 29±1. Proparacaine hydrochloride 0.5% (1-2 drops) was delivered to each eye prior to measurements. IOP was evaluated with a Medtronic Solan, Model 30 classic pneumatonometer on conditioned rabbits. A three-point diurnal curve was established: Intraocular pressure was recorded at 8 a.m., 12 p.m., and 4 p.m., with a ±1 hour range for each of these times.

Gross ocular observations were performed once weekly.

Ophthalmic observations (slit lamp and indirect ophthalmoscopy) were performed on both eyes of each remaining animal on Days 2, 8±1, 15±1, 22±1, and 29±1. Observations were performed by the same veterinary ophthalmologist for all timepoints.

Blood (at least 0.5 mL) was collected from each animal via ear vein or cardiac puncture prior to euthanasia. Animals were weighed and anesthetized with an intravenous injection of a ketamine/xylazine cocktail (87 mg/mL ketamine, 13 mg/mL xylazine) at a volume of 0.1 mL/kg. Animals were euthanized with an intravenous injection of commercial euthanasia solution following blood collection.

Each approximate 0.5-mL blood sample was collected into a single, pre-labeled $K_3$ EDTA tube. Each tube was inverted 5-10 times to ensure adequate mixing of blood and anticoagulant. The tubes were then placed on ice. Using a glass pipette, duplicate 0.2-mL aliquots of whole blood were transferred into silanized round bottom 13×100 mm screw top glass centrifuge tubes with Teflon caps containing 2.5 mL of 50% acetonitrile/50% methanol (high purity). Tubes were then vortexed. Blood samples were stored temporarily on wet ice until transferred to a freezer (at or below −20° C.) Samples were maintained at or below −20° C. until submitted for testing.

For eyes designated for pharmacokinetics analysis, aqueous humor samples were collected from all eyes before the eyes were enucleated, and the volume collected was measured and recorded. Both globes were enucleated and frozen in liquid nitrogen (at −20° C. or below).

Eyes were dissected as follows: The iris/ciliary body (ICB) was collected first, followed by collection of the vitreous humor (VH) and the retina.

Tissue weights were recorded for all tissues collected from all eyes. Careful attention was used to ensure that there is no cross contamination during dissection.

Aqueous humor (AH) and VH were placed in silanized amber screw-cap glass vials (3 mL) with Teflon or other inert washer. ICB and retina samples were placed in silanized round bottom 13×100 mm screw top glass centrifuge tubes with Teflon caps. Collected tissues were frozen on dry ice immediately after collection. All samples were stored at −20° C. or below until analysis.

The acceptable time ranges for sample collections (blood and ocular tissues) are summarized in the following Table 9:

TABLE 9

| Scheduled Collection Time (Day) | Acceptable Time Range |
| --- | --- |
| 2 | ±0 days |
| 8, 15, 22, 29 | ±1 day |

Ocular tissue samples collected for pharmacokinetics were analyzed using a validated LC-MS/MS method. Samples were quantified with AH, ICB, VH and retina assay range for bimatoprost and a bimatoprost metabolite of 0.1 ng or ng/mL. Assay range for blood was 0.125 and 0.25 ng/mL for bimatoprost and the bimatoprost metabolite, respectively.

Following subconjunctival injection of the microparticles, mainly the bimatoprost metabolite was detected in the AH, and bimatoprost was detected in blood. Both bimatoprost and the bimatoprost metabolite were detected in the ICB, VH and retina. Contralateral diffusion of bimatoprost and the bimatoprost metabolite to the untreated eyes was detected in the ICB and VH. In contrast, no drug levels were detected in all tissues at all timepoints (Day 1-14) following subconjunctival injection of 300 μg bimatoprost solution. Significantly, the subconjunctival bimatoprost microparticles caused little or no eye redness (hyperemia) in the rabbits. This is an unexpected advantage, for example, since topical administration of bimatoprost-containing eye drops can cause instances of hyperemia.

For all formulations dosed either at 300 μg or 600 μg dose, AH bimatoprost levels were detected at below the limit of quantification (BLQ) (<0.1 ng/mL) for all timepoints. Similar levels were detected for the bimatoprost metabolite, with the exception of a few treated eyes which had an AH level slightly above the BLQ level.

For all formulations dosed either at 300 μg or 600 μg dose, bimatoprost and bimatoprost metabolite were detected in the ICB at the earliest timepoint of Day 1. Only one formulation resulted in drug levels beyond Day 1 up to Day 21.

For all formulations dosed either at 300 μg or 600 μg dose, bimatoprost was detected in the VH at the earliest timepoint of about Day 1. Only one formulation, Formulation 3, resulted in drug levels beyond Day 1 up to Day 21. The bimatoprost VH maximum concentration for this formulation dosed at 300 μg and 600 μg was 1.73 ng/mL (Day 1) and 13.4 ng/mL (Day 1), respectively.

For all formulations dosed either at 300 μg or 600 μg dose, bimatoprost and bimatoprost metabolite were detected in the retina at the earliest timepoint of Day 1. Only one formulation resulted in bimatoprost levels beyond Day 1 up to Day 7, Formulation 3 (300 μg) and beyond Day 1 up to Day 21, Formulation 3 (600 μg). The bimatoprost retinal maximum concentration for this formulation dosed at 300 μg and 600 μg bimatoprost was 101 ng/g (Day 7) and 289 ng/g (Day 1), respectively.

For all formulations administered at either 300 μg or 600 μg dose, blood drug levels were mainly at BLQ.

No mortality or drug-related effects on ophthalmic observations, body weight, or gross ocular observations were observed up to 1 month after administration.

This study shows that bimatoprost microparticles can be administered subconjunctivally to produce concentrations, for example therapeutically effective concentrations, of bimatoprost/metabolite in various portions of the eye for periods of time of at least about 1 week or at least about 2 weeks or at least about 3 weeks. Thus, these subconjunctival injected bimatoprost microspheres can be used to effectively treat glaucoma. The fact that a relatively large amount of the bimatoprost administered subconjunctivally was passed to the posterior chamber, as bimatoprost or the bimatoprost metabolite is significant, for example, in treating conditions/diseases of the retina, for example, dry age-related macular degeneration, as well as other retinal conditions/diseases.

Example 9

Subconjunctivally Injected Bimatoprost Microspheres to Treat Glaucoma

A 56 year old male suffering from glaucoma in both eyes receives a subconjunctival injection of microspheres containing bimatoprost and a combination of a PLA and PLGA within the subconjunctival space of each eye. The microspheres contain 4% bimatoprost, and 40 mg of microspheres are used for each injection. In about two days, the patient reports a substantial relief in ocular comfort. Determination of intraocular pressure (IOP) reveals that the IOP has decreased in each eye, the average intraocular pressure measured at 8:00 AM has decreased from 28 mm Hg to 14.3 mm Hg. The patient is monitored every other day for about 1 month. Intraocular pressure levels remain below 15 mm Hg for this period of time, and the patient reports reduced ocular discomfort. Little or no ocular hyperemia is observed.

Example 10

Oil in Water Method for Making Bimatoprost Microspheres

This example describes an oil in water emulsion evaporation for making microparticles that include a prostamide derivative encapsulated by a biodegradable polymer. In the specific example, bimatoprost was used as the prostamide derivative. The procedures outlined herein can be used to make encapsulated microparticles of other prostamide derivatives as well.

Preparation of bimatoprost containing microspheres is difficult due to a lack of a significant solubility differential of bimatoprost in water as well as in many organic phases such as ethyl acetate and methylene chloride. When known oil in water emulsion evaporation processes are used most of the bimatoprost escapes into the aqueous phase. This Example sets forth an oil in water emulsion evaporation process which has been successfully used to make bimatoprost containing PLGA microspheres. An oil in water process is used in which an excess amount of the bimatoprost is added to the aqueous phase so as to saturate the aqueous phase to thereby prevent or reduce escape of the bimatoprost from the aqueous phase, with the result of higher drug loading (up to about 10 wt %) in the microspheres made.

The following process was used to make biodegradable bimatoprost microspheres using Poly(D,L-lactide-co-glycolide) (PLGA). An emulsion/solvent evaporation technique was used. The continuous or aqueous non-solvent phase was saturated with bimatoprost to prevent loss of bimatoprost from the polymer phase and increase loading efficiency. As drug diffuses away from the polymer phase during microsphere hardening counter-diffusion of drug into the polymer phase from the saturated aqueous phase minimizes loss of the bimatoprost.

Bimatoprost loaded PLGA microspheres were prepared using the emulsion/evaporation procedure as follows: (1) 1 gram of PLGA (75:25) was combined with 1 gram of bimatoprost in 60 milliliters of dichloromethane (an organic solvent) (this formed the polymer phase; also referred to as the oil phase or as the organic phase); (2) 10 grams of polyvinyl alcohol ("PVA") was combined with 1 gram of bimatoprost in 300 milliliters of water to thereby form a saturated aqueous phase (aqueous phase); (3) the polymer phase was emulsified with the aqueous phase by drop wise addition of the polymer phase into the aqueous phase under continuous mixing with a high shear impeller; (4) the resulting PLGA microspheres were hardened through the evaporation of the dichloromethane by stirring the emulsion in an open beaker for 24 hours; (5) the hardened microspheres were separated from the remaining PVA solution by centrifugation; (6) the microsphere pellets were suspended and washed 3 times with water; (7) the microspheres were dried under vacuum at 45° C. overnight; (8) the dried microspheres were sized to 38 microns through sieves.

The percent of bimatoprost loaded into the microspheres by this process was analyzed by HPLC to be 11.91%. The particle size distribution of the microspheres was determined to have a mean of 8.7 microns. The percent release of bimatoprost from the microspheres was assessed using dialysis.

In variants of this process the solvent used can be, for example, ethyl acetate or methylene chloride. The PLGA polymer used can be, for example, 50:50 DL-PLG acid, 65:35 DL-PLG, 65:35 COOH, 75:25 COOH or 75:25 lauryl ester capped. DL-PLG acid 50:50 DL-PLG acid. The mean microparticle diameter can be from about 5 microns and about 20 microns.

In another variant of our an oil in water emulsion evaporation process for making microparticles that include a prostamide derivative encapsulated by a biodegradable polymer, a solid bimatoprost can be present in the emulsion during preparation. In such a variant of our process, the drug (bimatoprost) concentration exceeds its solubilities in both the aqueous and the organic phases and the drug is present as microfine particles in both phases as well. As the PLGA hardens when the organic phase evaporates, the drug can be captured as microfine particles as well as from precipitation.

Significantly, bimatoprost encapsulation within PLGA allows terminal sterilization with gamma radiation (i.e. by exposing the microparticles to gamma radiation at a dose of about 25-35 kGy) with low to moderate impact on the biological stability of the encapsulated bimatoprost.

All references, articles, publications and patents and patent applications cited herein are incorporated by reference in their entireties.

While this invention has been described with respect to various specific examples and embodiments, it is to be understood that the invention is not limited thereto and that it can be variously practiced within the scope of the following claims.

We claim:

1. A population of microparticles comprising a polymeric component encapsulating travoprost in the form of oil-in-water emulsified microparticles.

2. The population of claim 1, wherein the polymeric component comprises a poly(lactide-co-glycolide) copolymer.

3. The population of claim 1 which is terminally sterilized.

4. The population of claim 3, wherein at least 80% of the travoprost remains stable after the sterilization.

5. The population of claim 1 having a mean particle diameter from about 30 μm to about 50 μm.

6. The population of claim 1, wherein the maximum particle diameter is less than about 200 μm.

7. The population of claim 1, wherein the microparticles have a release rate of the travoprost of about 0.7% per day in vitro.

8. The population of claim 1, wherein the travoprost comprises about 10% wt/wt of the microparticles.

9. The population of claim 1, wherein the travoprost comprises about 5% wt/wt of the microparticles.

10. A method of treating an ocular condition in an eye of a patient, comprising the step of placing the population of claim 1 in an eye of a patient.

11. The method of claim 10 which is effective to treat glaucoma.

12. The method of claim 10 which is effective to decrease intraocular pressure.

\* \* \* \* \*

UNITED STATES PATENT AND TRADEMARK OFFICE
CERTIFICATE OF CORRECTION

Page 1 of 4

PATENT NO.         : 9,707,238 B2
APPLICATION NO.    : 14/822646
DATED              : July 18, 2017
INVENTOR(S)        : James Chang et al.

It is certified that error appears in the above-identified patent and that said Letters Patent is hereby corrected as shown below:

On the Title Page

On the page 4, in Column 1, under "Other Publications", Line 11, delete "Polyactides" and insert -- Polylactides --, therefor.

On the page 4, in Column 1, under "Other Publications", Line 51, delete "Uveites," and insert -- Uveitis, --, therefor.

On the page 4, in Column 1, under "Other Publications", Line 54, delete "Pharrnacokinetics" and insert -- Pharmacokinetics --, therefor.

On the page 4, in Column 2, under "Other Publications", Line 4, delete "Photocoagulatio" and insert -- Photocoagulation --, therefor.

On the page 4, in Column 2, under "Other Publications", Line 6, delete "Ophthalmal," and insert -- Ophthalmol, --, therefor.

On the page 4, in Column 2, under "Other Publications", Line 15, delete "Scient," and insert -- Science, --, therefor.

On the page 4, in Column 2, under "Other Publications", Line 18, delete "Dexamethason," and insert -- Dexamethasone, --, therefor.

On the page 4, in Column 2, under "Other Publications", Line 23, delete "Curent" and insert -- Current --, therefor.

On the page 4, in Column 2, under "Other Publications", Line 25, delete "2-methoxyoestradiol" and insert -- 2-methoxyestradiol --, therefor.

Signed and Sealed this
Nineteenth Day of September, 2017

Joseph Matal
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 9,707,238 B2

On the page 4, in Column 2, under "Other Publications", Line 25, delete "Angiogeneses" and insert -- Angiogenesis --, therefor.

On the page 4, in Column 2, under "Other Publications", Line 45, delete "Plugof" and insert -- Plug of --, therefor.

On the page 4, in Column 2, under "Other Publications", Line 50, delete "Adrenocotical" and insert -- Adrenocortical --, therefor.

On the page 4, in Column 2, under "Other Publications", Line 61, delete "Formaton" and insert -- Formation --, therefor.

On the page 5, in Column 1, under "Other Publications", Line 10, delete "Polyactic" and insert -- Polylactic --, therefor.

On the page 5, in Column 1, under "Other Publications", Line 22, delete "Micoencapsulaton" and insert -- Microencapsulation --, therefor.

On the page 5, in Column 1, under "Other Publications", Line 22, delete "poly (L-lactic acid)" and insert -- poly(L-lactic acid) --, therefor.

On the page 5, in Column 1, under "Other Publications", Line 60, delete "5-Fluorouacil," and insert -- 5-Fluorouracil, --, therefor.

On the page 5, in Column 2, under "Other Publications", Line 10, delete "(Polyactates" and insert -- (Polylactates --, therefor.

On the page 5, in Column 2, under "Other Publications", Line 14, delete "Estratopones," and insert -- Estratropones, --, therefor.

On the page 5, in Column 2, under "Other Publications", Line 20, delete "Outrech," and insert -- Outreach, --, therefor.

On the page 5, in Column 2, under "Other Publications", Line 21, delete "Resorable" and insert -- Resorbable --, therefor.

On the page 5, in Column 2, under "Other Publications", Line 27, delete "Neuropathis:" and insert -- Neuropathies: --, therefor.

On the page 5, in Column 2, under "Other Publications", Line 39, delete "Transcleral" and insert -- Transscleral --, therefor.

On the page 5, in Column 2, under "Other Publications", Line 50, delete "Antiangionic"

and insert -- Antiangiogenic --, therefor.

On the page 5, in Column 2, under "Other Publications", Line 73, delete "Ophthamol." and insert -- Ophthalmol. --, therefor.

On the page 6, in Column 1, under "Other Publications", Line 3, delete "Clatide" and insert -- lactide --, therefor.

On the page 6, in Column 1, under "Other Publications", Line 16, delete "al," and insert -- al., --, therefor.

On the page 6, in Column 1, under "Other Publications", Line 17, delete "Elevatioin" and insert -- Elevation --, therefor.

On the page 6, in Column 1, under "Other Publications", Line 17, delete "Hisopathological" and insert -- Histopathological --, therefor.

On the page 6, in Column 1, under "Other Publications", Line 19, delete "Prostagladin" and insert -- Prostaglandin --, therefor.

On the page 6, in Column 1, under "Other Publications", Line 44, delete "Poly(actide-co-glycolide)" and insert -- Poly(lactide-co-glycolide) --, therefor.

On the page 6, in Column 2, under "Other Publications", Line 20, delete "60/567339," and insert -- 60/567,339, --, therefor.

On the page 6, in Column 2, under "Other Publications", Line 34, delete "Interferenms" and insert -- Interferences --, therefor.

On the page 6, in Column 2, under "Other Publications", Line 62, delete "Neuoprotection" and insert -- Neuroprotection --, therefor.

In the Specification

In Column 2, Line 64, after "No." insert -- (USSN) --.

In Column 3, Line 34, delete "ethylheptenamide," and insert -- ethylheptanamide, --, therefor.

In Column 6, Line 39, after "of" delete "trans".

In Column 11, Line 7, delete "-(CH$_2$)-R$^7$" and insert -- -(CH$_2$)$_m$R$^7$ --, therefor.

In Column 14, Line 26, delete "9- and/or" and insert -- 9-and/or --, therefor.

CERTIFICATE OF CORRECTION (continued)
U.S. Pat. No. 9,707,238 B2

In Column 14, Line 26, delete "11- and/or" and insert -- 11-and/or --, therefor.

In Column 16, Line 45, delete "0-1000," and insert -- 0-100%, --, therefor.

In Column 25, Line 8, delete "Telangiectasis," and insert -- Telangiectasia, --, therefor.

In Column 25, Line 9, delete "Branch," and insert -- Branch --, therefor.

In Column 29, Line 41, delete "1513" and insert -- 15β --, therefor.

In Column 34, Line 64, delete "150-W," and insert -- 150-μL --, therefor.